(12) United States Patent
Smith et al.

(10) Patent No.: US 12,156,978 B2
(45) Date of Patent: Dec. 3, 2024

(54) INTRAVASCULARLY DELIVERED BLOOD PUMPS AND ASSOCIATED DEVICES, SYSTEMS, AND METHODS

(71) Applicant: NUPULSECV, INC., Raleigh, NC (US)

(72) Inventors: Robert M. Smith, Raleigh, NC (US); Guruprasad Anapathur Giridharan, Lousiville, KY (US); Duane Pinto, Newton, MA (US); Joshua Ryan Woolley, Pittsburgh, PA (US); Brian Howard Novack, Beverly Hills, CA (US); Douglas Altschuler, Raleigh, NC (US)

(73) Assignee: NUPULSECV, INC., Raleigh, NC (US)

( * ) Notice: Subject to any disclaimer, the term of this patent is extended or adjusted under 35 U.S.C. 154(b) by 1049 days.

(21) Appl. No.: 16/876,110

(22) Filed: May 17, 2020

(65) Prior Publication Data

US 2020/0360663 A1 Nov. 19, 2020

Related U.S. Application Data

(60) Provisional application No. 62/849,646, filed on May 17, 2019.

(51) Int. Cl.
*A61M 25/01* (2006.01)
*A61M 25/00* (2006.01)
(Continued)

(52) U.S. Cl.
CPC ........ *A61M 25/0133* (2013.01); *A61M 25/09* (2013.01); *A61M 60/13* (2021.01);
(Continued)

(58) Field of Classification Search
None
See application file for complete search history.

(56) References Cited

U.S. PATENT DOCUMENTS

| 3,585,983 A | 6/1971 | Kantrowitz et al. |
| 3,692,018 A | 9/1972 | Goetz et al. |

(Continued)

FOREIGN PATENT DOCUMENTS

| DE | 3722161 A1 | 1/1989 |
| EP | 0228787 A1 | 7/1987 |

(Continued)

OTHER PUBLICATIONS

Bard Dynaflow Instructions for Use (Dec. 2007), 40 pages.
(Continued)

*Primary Examiner* — Carl H Layno
*Assistant Examiner* — Manolis Pahakis
(74) *Attorney, Agent, or Firm* — LOEB & LOEB LLP

(57) ABSTRACT

Intravascularly delivered blood pumps and associated devices, systems, and methods, are disclosed herein. A system for intravascularly implanting a blood pump in accordance with embodiments of the present technology can include, for example, an elongated delivery dilator having a first end portion, a second end portion, and a lumen extending between the first end portion and the second end portion. The elongated delivery dilator is configured to advance over a guidewire positioned within the patient's vasculature and to extend through the patient's vasculature between a first blood vessel and a second blood vessel. A pump assembly includes an expandable member and a driveline. The expandable member is configured to be positioned in a patient's descending aorta to provide circulatory support to the patient's heart.

25 Claims, 20 Drawing Sheets

(51) Int. Cl.
| | |
|---|---|
| *A61M 25/09* | (2006.01) |
| *A61M 39/06* | (2006.01) |
| *A61M 60/13* | (2021.01) |
| *A61M 60/139* | (2021.01) |
| *A61M 60/178* | (2021.01) |
| *A61M 60/247* | (2021.01) |
| *A61M 60/295* | (2021.01) |
| *A61M 60/497* | (2021.01) |
| *A61M 60/508* | (2021.01) |
| *A61M 60/585* | (2021.01) |
| *A61M 60/843* | (2021.01) |
| *A61M 60/857* | (2021.01) |
| *A61M 60/865* | (2021.01) |

(52) U.S. Cl.
CPC ........ *A61M 60/139* (2021.01); *A61M 60/178* (2021.01); *A61M 60/247* (2021.01); *A61M 60/295* (2021.01); *A61M 60/497* (2021.01); *A61M 60/508* (2021.01); *A61M 60/585* (2021.01); *A61M 60/843* (2021.01); *A61M 60/857* (2021.01); *A61M 60/865* (2021.01); *A61M 25/0043* (2013.01); *A61M 2025/0059* (2013.01); *A61M 25/0108* (2013.01); *A61M 2025/09008* (2013.01); *A61M 2025/09141* (2013.01); *A61M 39/06* (2013.01)

(56) References Cited

U.S. PATENT DOCUMENTS

| | | | |
|---|---|---|---|
| 3,720,199 A | | 3/1973 | Rishton et al. |
| 3,924,634 A | * | 12/1975 | Taylor ............... A61M 25/1002 |
| | | | 604/100.01 |
| 3,964,470 A | | 6/1976 | Trombley |
| 4,038,625 A | | 7/1977 | Tompkins et al. |
| 4,051,840 A | | 10/1977 | Kantrowitz et al. |
| 4,185,617 A | | 1/1980 | Hutchins |
| 4,276,874 A | | 7/1981 | Wolvek et al. |
| 4,327,709 A | | 5/1982 | Hanson et al. |
| 4,527,549 A | | 7/1985 | Gabbay |
| 4,540,404 A | | 9/1985 | Wolvek |
| 4,634,430 A | | 1/1987 | Polaschegg |
| 4,785,795 A | | 11/1988 | Singh |
| 4,902,272 A | | 2/1990 | Milder et al. |
| 4,994,018 A | | 2/1991 | Saper |
| 5,052,934 A | | 10/1991 | Carey et al. |
| 5,098,397 A | | 3/1992 | Svensson et al. |
| 5,147,318 A | | 9/1992 | Hohn |
| 5,176,619 A | | 1/1993 | Segalowitz |
| 5,350,413 A | | 9/1994 | Miller |
| 5,433,700 A | | 7/1995 | Peters |
| 5,509,902 A | | 4/1996 | Raulerson |
| 5,683,347 A | | 11/1997 | Miyata |
| 5,782,645 A | | 7/1998 | Stobie |
| 5,820,542 A | | 10/1998 | Dobak, III et al. |
| 5,833,655 A | | 11/1998 | Freed et al. |
| 5,876,367 A | | 3/1999 | Kaganov et al. |
| 5,904,646 A | | 5/1999 | Jarvik |
| 6,030,336 A | | 2/2000 | Franchi |
| 6,132,363 A | | 10/2000 | Freed et al. |
| 6,210,318 B1 | | 4/2001 | Lederman |
| 6,245,008 B1 | | 6/2001 | Leschinsky et al. |
| 6,406,422 B1 | | 6/2002 | Landesberg |
| 6,453,195 B1 | | 9/2002 | Thompson |
| 6,468,200 B1 | | 10/2002 | Fischi |
| 6,530,876 B1 | | 3/2003 | Spence |
| 6,945,926 B2 | | 9/2005 | Trumble |
| 6,961,448 B2 | | 11/2005 | Nichols et al. |
| 7,059,338 B1 | | 6/2006 | Kincaid et al. |
| 7,374,531 B1 | | 5/2008 | Kantrowitz |
| 7,468,050 B1 | | 12/2008 | Kantrowitz |
| 7,494,459 B2 | | 2/2009 | Anstadt et al. |
| 7,520,850 B2 | | 4/2009 | Brockway |
| 7,574,262 B2 | | 8/2009 | Haugland et al. |
| 7,632,263 B2 | | 12/2009 | Denoth et al. |
| 7,666,167 B2 | | 2/2010 | Bierman |
| 7,766,881 B2 | | 8/2010 | Reinmann |
| 7,892,162 B1 | | 2/2011 | Jeevanandam et al. |
| 7,935,096 B2 | | 5/2011 | Johannsson et al. |
| 7,988,674 B2 | | 8/2011 | Adams et al. |
| 8,066,628 B1 | * | 11/2011 | Jeevanandam ..... A61M 60/497 |
| | | | 600/17 |
| 8,152,769 B2 | | 4/2012 | Douglas |
| 8,323,174 B2 | | 12/2012 | Jeevanandam et al. |
| 8,326,421 B2 | | 12/2012 | Jeevanandam et al. |
| 8,574,204 B2 | | 11/2013 | Bourne et al. |
| 8,608,637 B2 | | 12/2013 | Jeevanandam et al. |
| 8,684,905 B2 | | 4/2014 | Jeevanandam et al. |
| 9,125,981 B2 | | 9/2015 | Mann et al. |
| 9,265,871 B2 | | 2/2016 | Jeevanandam et al. |
| 9,592,328 B2 | | 3/2017 | Jeevanandam et al. |
| 9,839,734 B1 | | 12/2017 | Menon |
| 10,137,230 B2 | | 11/2018 | Novack |
| 2003/0074144 A1 | | 4/2003 | Freed et al. |
| 2003/0083539 A1 | | 5/2003 | Leschinsky |
| 2003/0163147 A1 | * | 8/2003 | Rabiner ........... A61B 17/22012 |
| | | | 606/159 |
| 2004/0152945 A1 | | 8/2004 | Kantrowitz et al. |
| 2004/0249361 A1 | | 12/2004 | Denoth |
| 2005/0014991 A1 | | 1/2005 | Sugiura |
| 2005/0192604 A1 | | 9/2005 | Carson et al. |
| 2006/0063965 A1 | | 3/2006 | Aboul-Hosn et al. |
| 2007/0191779 A1 | | 8/2007 | Shubayev |
| 2008/0183136 A1 | | 7/2008 | Lenker et al. |
| 2009/0131741 A1 | | 5/2009 | Kantrowitz |
| 2010/0228077 A1 | * | 9/2010 | Lenker ............. A61M 25/0662 |
| | | | 600/18 |
| 2012/0108885 A1 | | 5/2012 | Jeevanandam et al. |
| 2012/0108886 A1 | | 5/2012 | Jeevanandam et al. |
| 2012/0149970 A1 | | 6/2012 | Jeevanandam et al. |
| 2012/0149971 A1 | | 6/2012 | Jeevanandam et al. |
| 2013/0066365 A1 | | 3/2013 | Belson et al. |
| 2013/0331638 A1 | | 12/2013 | Cameron et al. |
| 2015/0051436 A1 | * | 2/2015 | Spanier ............ A61M 60/237 |
| | | | 600/16 |
| 2015/0065786 A1 | | 3/2015 | Jeevanandam et al. |
| 2015/0157842 A1 | | 6/2015 | Gill |
| 2015/0258261 A1 | | 9/2015 | Novack |
| 2016/0136343 A1 | | 5/2016 | Anagnostopoulos |
| 2016/0158426 A1 | | 6/2016 | Jeevanandam et al. |
| 2016/0175502 A1 | * | 6/2016 | McSweeney ....... A61M 60/216 |
| | | | 623/3.26 |
| 2017/0021071 A1 | * | 1/2017 | Cotter .................. A61M 60/822 |
| 2017/0173237 A1 | * | 6/2017 | Pfeifer .................. A61M 25/09 |
| 2017/0216506 A1 | * | 8/2017 | Jeevanandam ....... A61M 25/09 |
| 2018/0055981 A1 | * | 3/2018 | Smith .................. A61M 60/867 |
| 2018/0099078 A1 | * | 4/2018 | Tuseth ................ A61M 60/216 |
| 2019/0184077 A1 | | 6/2019 | Novack |
| 2020/0069855 A1 | * | 3/2020 | Matthes ............. A61M 60/878 |

FOREIGN PATENT DOCUMENTS

| | | | | |
|---|---|---|---|---|
| EP | 2548593 A1 | * | 1/2013 | ........... A61M 1/106 |
| GB | 2050175 A | | 8/1980 | |
| JP | 2002518106 A | | 6/2002 | |
| JP | 2005000434 A | | 1/2005 | |
| WO | 91/11208 A1 | | 8/1991 | |
| WO | 2012101267 A1 | | 8/2012 | |

OTHER PUBLICATIONS

BioSpan: "Segmented Polyurethane (SPU)" www.dsm.com, DSM, 2014. www.dsm.com/markets/medical/en_US/products-page/products-biostable-polyurethanes/product-pu-biospan-spu.htm; 2 pages.

Chen, Z., R. Ward, Y. Tian, F. Malizia, D. H. Gracias, Y. R. Shen, and G. A. Somorjai, Interation of fibrinogen with surfaces of end-group-modified polyurethanes: a surface-specific sum-frequency-generation vibrational spectroscopy study. J. Biomed. Mater. Res., 62 (2002):254-264.

(56) References Cited

OTHER PUBLICATIONS

EPO, Examination Report for European Patent Application No. 15765631.5. Mail Date: Oct. 1, 2019. 4 pages.
EPO, Extended European Search Report for European Patent Application No. 17844423.8. Mail Date: Feb. 18, 2020. 7 pages.
EPO, Supplemental European Search Report for European Patent Application No. 15765631.5. Mail Date: Oct. 26, 2017. 7 pages.
International Search Report issued on Nov. 9, 2017, regarding PCT/US2017/048429.
International Search Report and Written Opinion for PCT/US2010/053779 dated Jul. 1, 2011.
International Search Report (ISR) from Related International Application No. PCT/US2014/053943 Jan. 6, 2015.
Jeevanandam et al. "Circulatory Assistance with a Permanent Implantable IABP: Initial Human Experience" Circulation, 2002, 106:I-183-I-188.
Kantrowitz et al. "A Mechanical Auxiliary Ventricle: Histologic Responses to Long-Term, Intermittent Pumping in Calves" ASAIO Journal, 1995, 41(34), M340-M345.
Li et al. "The Kantrowitz CardiovadTM System Can Be Deactivated for Two Months and Reactivated Without Thromboembolism" ASAIO Journal, 2000, vol. 46, No. 2, p. 205.
USPTO, International Search Report and Written Opinion for International Patent Application No. PCT/US2014/053943. Mail Date: Jan. 23, 2015. 9 pages.
USPTO, International Search Report and Written Opinion for International Patent Application No. PCT/US2015/020803. Mail Date: Jun. 25, 2015. 14 pages.

\* cited by examiner

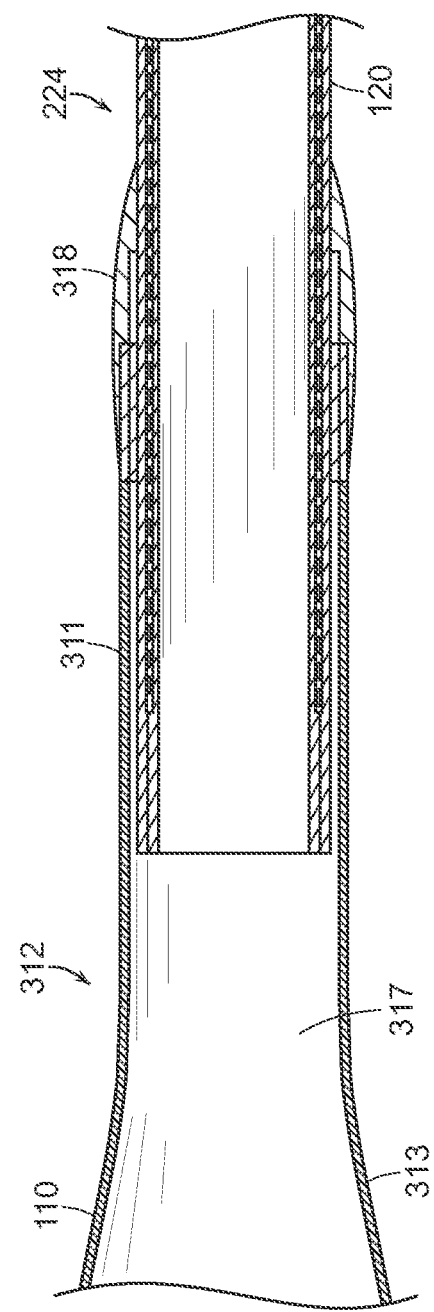

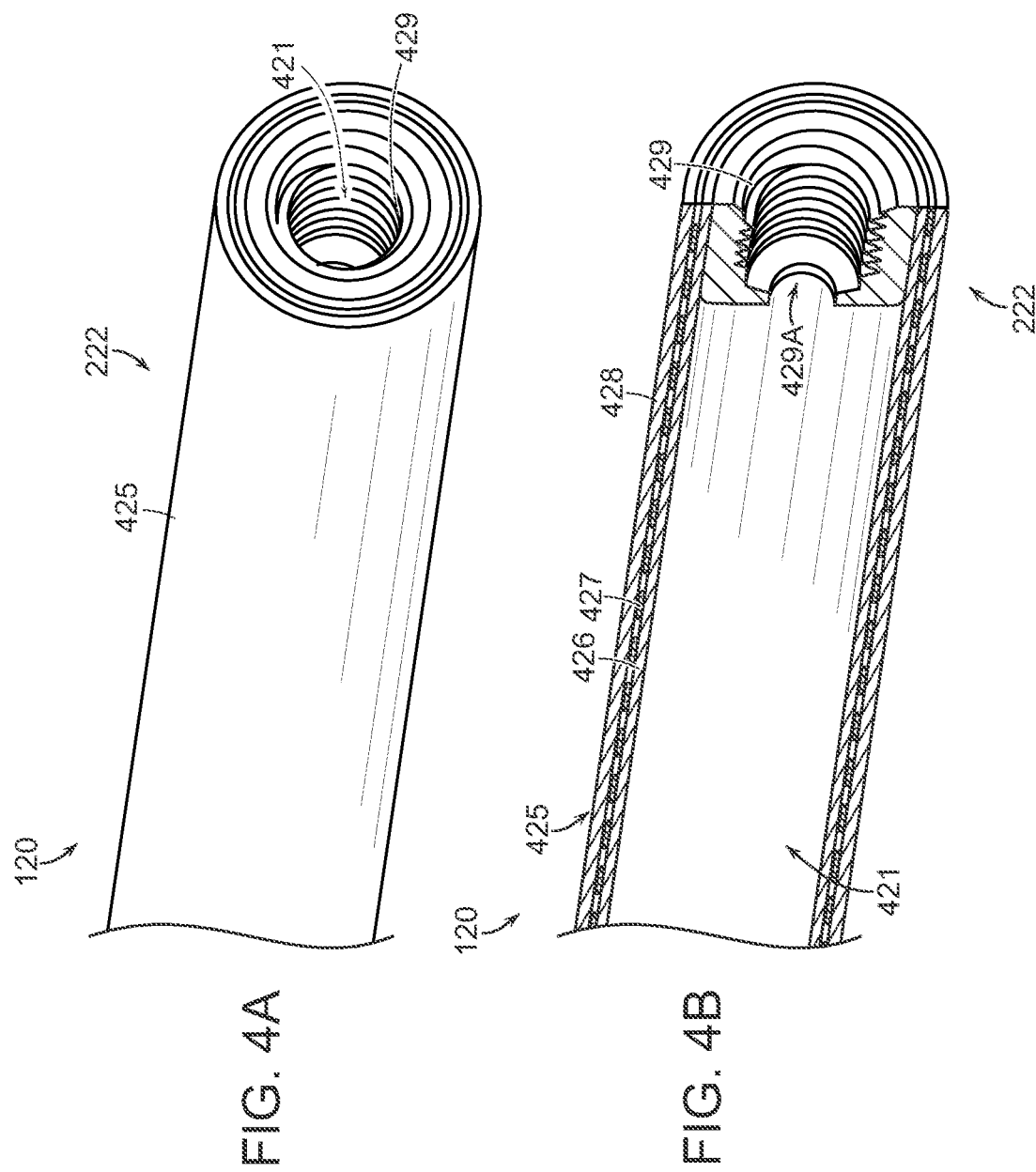

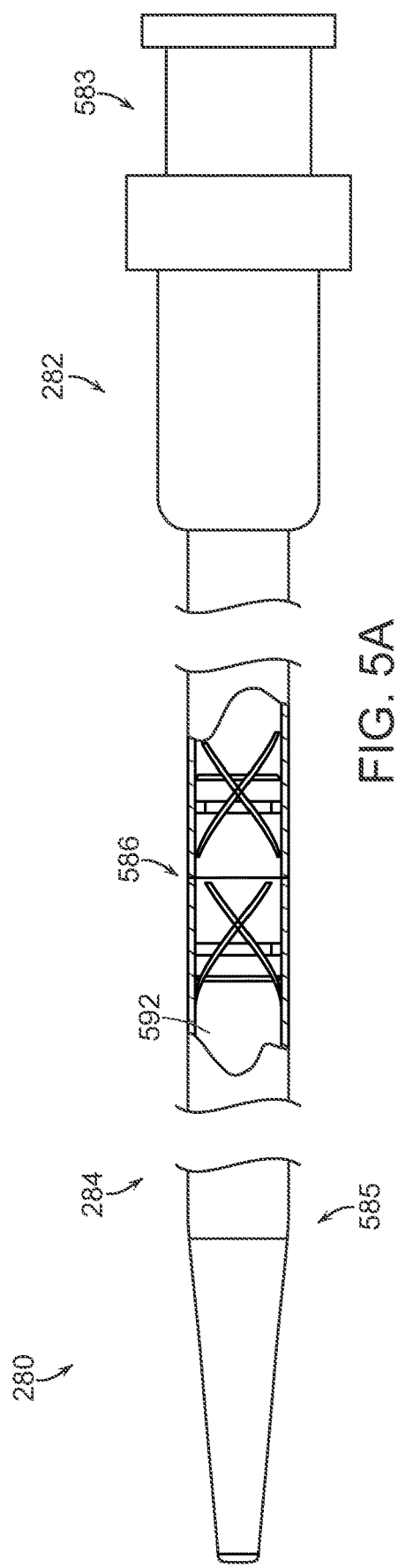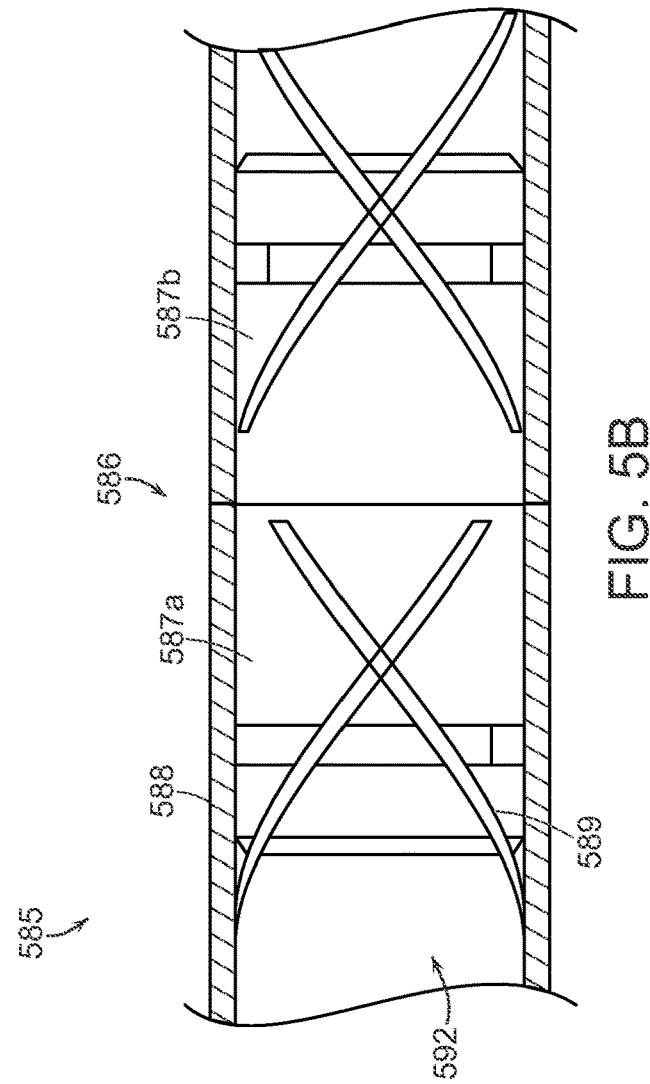
FIG. 5A
FIG. 5B

INTRAVASCULARLY DELIVERED BLOOD PUMPS AND ASSOCIATED DEVICES, SYSTEMS, AND METHODS

CROSS-REFERENCE TO RELATED APPLICATION(S)

The present application claims priority to U.S. Provisional Patent Application No. 62/849,646, titled PERCUTANEOUS BLOOD PUMP AND ASSOCIATED DEVICES, SYSTEMS, AND METHODS, filed May 17, 2019, the disclosure of which is incorporated herein by reference in its entirety.

TECHNICAL FIELD

The present technology is directed to systems, device, and methods for treating heart failure, and in particular to methods for intravascularly implanting circulatory support systems and associated systems and methods.

BACKGROUND

The prevalence of heart failure is increasing worldwide and is an expensive burden on health care providers. Despite advances in medical care, prognosis for patients with heart failure remains poor, especially in patients having advanced stage heart failure. This is due in part to limited therapy options for such patients. For example, heart transplantation remains limited by the supply of donor organs, and the use of left ventricular assist devices (LVAD) is stagnant at approximately 5,000 implants per year due to, among other things, the requirement for major operative intervention and cardio-pulmonary bypass. Additionally, the high cost of LVAD has prevented the widespread adoption of these devices. For example, some countries have decided against funding the use of LVAD for long-term mechanical support of heart failure patients. While biventricular pacemakers are commonly used to treat early stage Class III heart failure patients, the use of left ventricular assist devices is limited to advanced Class IV patients, leaving a group of heart failure patients with limited to no treatment options.

BRIEF DESCRIPTION OF THE DRAWINGS

Many aspects of the present technology can be better understood with reference to the following drawings. The components in the drawings are not necessarily to scale, and instead emphasis is placed on illustrating clearly the principles of the present disclosure.

FIGS. 2H and 2I are flowcharts for a procedure for intravascularly explanting and/or exchanging one or more implanted components of the circulatory support system illustrated in FIG. 1 in accordance with embodiments of the present technology.

FIGS. 3A-3C are side and cross-sectional views, respectively, of an expandable member and a driveline configured in accordance with embodiments of the present technology.

FIGS. 4A and 4B are enlarged isometric and cross-sectional views, respectively, illustrating features of the driveline shown in FIGS. 3A-3C in accordance with embodiments of the present technology.

FIGS. 5A-5C are partial cutaway, side views of an elongated delivery dilator configured in accordance with embodiments of the present technology.

DETAILED DESCRIPTION

Figure 1:
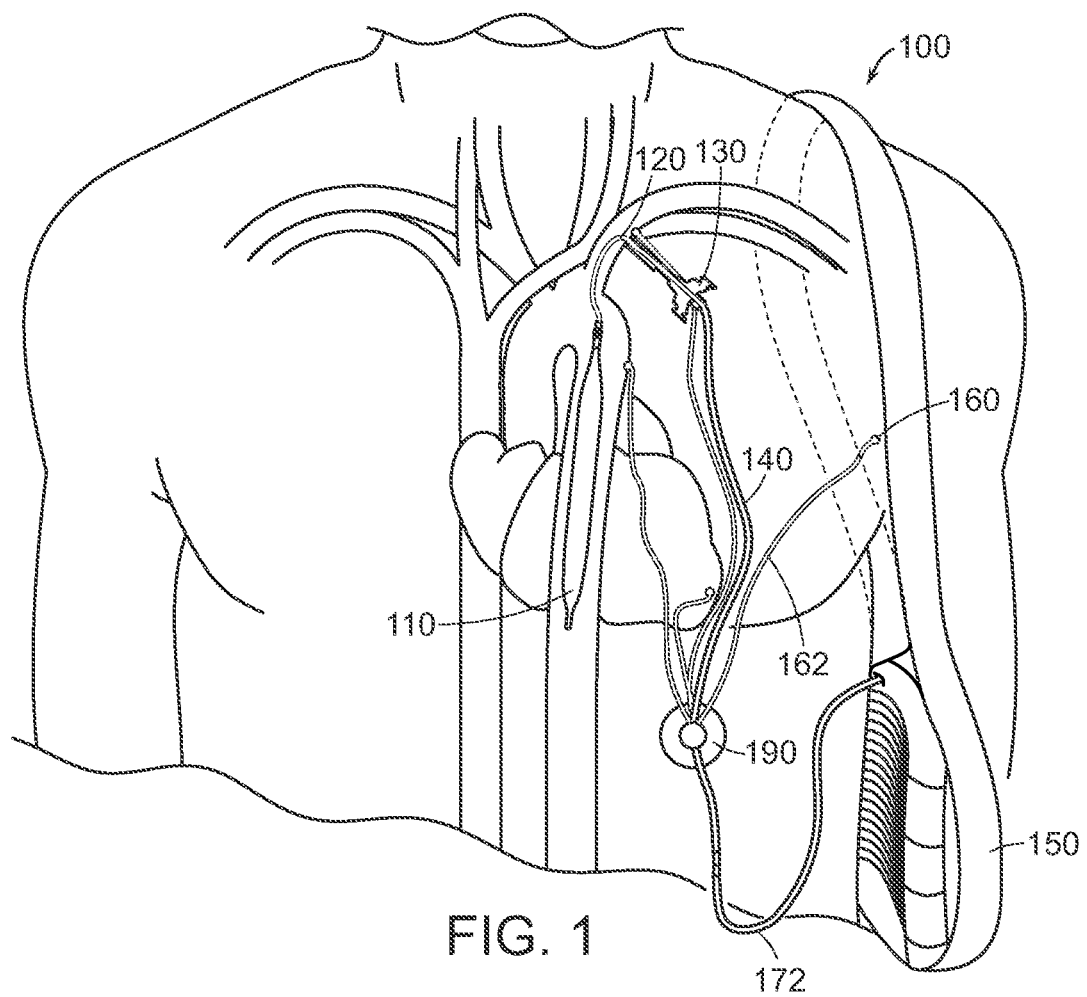
FIG. 1 illustrates an intravascular circulatory support system implanted within a patient's vasculature and configured in accordance with embodiments of the present technology.

The present technology provides circulatory support systems and devices, and methods for intravascularly implanting, retrieving, and replacing the same. In some embodiments, an intravascular delivery procedure begins by accessing both a subclavian artery (e.g., via an axillary artery) and a femoral artery of a patient, and advancing a guidewire through the patient's vasculature such that the guidewire extends between the subclavian and femoral arteries. The method continues by advancing an elongated delivery dilator over the guidewire such that the elongated delivery dilator extends between the subclavian and femoral arteries, with a first portion of the elongated delivery dilator externally accessible proximate to the subclavian artery and a second portion of the elongated delivery dilator externally accessible proximate to the femoral artery. The method further includes releasably attaching the second portion of the elongated delivery dilator to a first end region of a driveline that has a second end region coupled to a deflated intra-aortic balloon. By pulling on the first portion of the elongated delivery dilator near the subclavian artery, the elongated delivery dilator, the driveline, and the balloon move through the patient's vasculature in a direction opposite that of blood flow until the balloon is positioned at a target site within the patient's descending aorta. Circulatory support systems delivered using the intravascular delivery systems and procedures described herein are designed to provide long-term support to patient's suffering from heart failure.

Specific details of several embodiments of the technology are described below with reference to FIGS. 1-8B. Although many of the embodiments are described below with respect to delivery and use of intravascular ventricular assist devices ("iVAD") that position a balloon pump in the aorta to provide counterpulsation that helps move blood through the body, other applications and other embodiments in addition to those described herein are within the scope of the technology. For example, the delivery devices, systems, and methods described herein may be used to implant other devices in the aorta and/or at other target sites within the patient's vasculature. Additionally, several other embodiments of the technology can have different configurations, components, or procedures than those described herein, and features of the embodiments shown can be combined with one another. A person of ordinary skill in the art, therefore, will accordingly understand that the technology can have other embodiments with additional elements, or the technology can have other embodiments without several of the features shown and described below with reference to FIGS. 1-8B.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-8B.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to a "practitioner" refers to a medical professional, including physicians, physician assistants, nurse practitioners, and the like, that can perform procedures and/or portions thereof. The "practitioner" can also refer to automated devices for performing medical procedures, such as robotic arms. Furthermore, while certain procedures are described as being done by "a" practitioner, further reference to "the" practitioner does not necessarily indicate that the same practitioner is performing each described step of the procedure. In fact, the steps of the procedure may be performed by multiple different practitioners. Accordingly, the use of "a" and "the" before practitioner does not limit the scope of who is performing the described step.

Reference throughout this specification to relative terms such as, for example, "generally," "approximately," and "about" are used herein to mean the stated value plus or minus 10%.

The headings provided herein are for convenience only and do not interpret the scope or meaning of the claimed present technology.

Heart Failure and Circulatory Support Systems

Heart failure occurs when the heart is unable to maintain blood flow to meet the body's needs. This can occur if the heart cannot pump or fill adequately during contraction and relaxation, respectively. Heart failure is a common, costly, and potentially fatal condition. For example, heart failure currently affects about 6.5 million patients in the United States and is expected to increase by 46% by 2030. The stage/severity of heart failure can be defined using New York Heart Association (NYHA) classes, with NYHA Class I representing an early stage disease and NYHA Class IV representing a late stage disease. Current treatment options for heart failure depend on the stage of heart failure, and include, among other options, pharmacological therapy, cardiac resynchronization therapy (CRT), long-term mechanical circulatory support (e.g., left ventricular assist devices, or "LVAD"), and heart transplantation. Pharmacological therapy and CRT are typically used in relatively early stage cases (e.g., in patients with NYHA Class II or early NYHA Class III heart failure). However, these therapies typically only delay the progression of heart failure, meaning that even patients who initially respond to pharmacological therapy or CRT typically experience disease progression and require more advanced therapeutic interventions.

Prognosis for patients with heart failure remains poor: one-year mortality is about 15.0% for NYHA Class III patients and about 28.0% for NYHA Class IV patients. This is at least partially due to the limited number of treatment options available for patients with late NYHA Class III/early NYHA Class IV heart failure. For example, while heart transplantation offers the best opportunity for long-term survival in late NYHA Class IV patients, this option is limited due to the scarcity of donor organs (e.g., approximately 2000 per year in the US, 200 per year in Canada, and less than 100 per year in Japan). Accordingly, many NYHA Class III and Class IV patients must rely on other treatments. For example, some patients receive LVAD therapy as a bridge to heart transplant or as a standalone therapy. However, LVAD therapy has several inherent shortcomings that limit their widespread use. Current LVAD therapies are expensive (e.g., over $100,000), typically require a major surgical procedure to implant (typically a sternotomy or thoracotomy), typically require use of cardiopulmonary bypass during the implant procedure, and typically require blood products (e.g., about 10-12 units of blood products). LVAD therapies that are implanted through less-invasive means (e.g., intravascularly) are only used for short-term circulatory support. Furthermore, postoperative care of patients who receive a LVAD can be challenging and costly, and patient anxiety can be high because the devices cannot be shut off or lose power for more than a few minutes. LVAD therapy is also associated with several serious adverse events such as device failure, thrombosis, thromboembolism, stroke, infection, and bleeding. For at least these reasons, LVAD therapy is typically reserved for patients with end-stage heart failure who have limited options (e.g., late NYHA Class IV). This leaves a large percentage of heart failure patients who have cases that are too advanced for CRT but are not yet severe enough to justify LVAD therapy/heart transplantation (e.g., late NYHA Class III/early NYHA Class IV patients) without effective treatment options. There are currently about 1.6 million patients in the United States and about 3.9 million patients in Europe with late Class III/early Class IV heart failure, representing a large patient population with limited treatment options.

Another treatment option for heart failure is counterpulsation therapy using an intra-aortic balloon pump (IABP). Counterpulsation therapy is achieved by rapidly inflating a balloon positioned in the patient's aorta immediately after aortic valve closure (dicrotic notch) and rapidly deflating the balloon just before the onset of systole. The rapid inflation of the balloon increases the diastolic aortic pressure by 25-70%, augmenting end-organ and coronary perfusion. The rapid deflation of the balloon reduces the ejection pressure of the native ventricle, reducing afterload and left ventricular external work. Counterpulsation therapy has been shown to be effective in patients when their systolic aortic pressures are between about 40 and 80 mmHg, their native heart rates are between about 70-110 bpm, and the counterpulsation volume (i.e., balloon volume) is roughly equal to the stroke volume of the native left ventricle.

Counterpulsation therapy is an attractive therapy option because using an IABP is much simpler than implanting and using an LVAD and is associated with fewer adverse events. For example, a physician can implant an IABP without directly cannulating the heart. However, conventional counterpulsation systems implanted through minimally invasive procedures can only be used for short durations. This is this case for several reasons. For example, the arterial access (e.g., the femoral artery), the durability of the IABP, and biocompatibility issues can limit the use of IABP to short durations of less than about 14 days. Longer duration of IABP support (>14 days) can lead to an increase in the frequency of vascular complications, infections, and bleeding. Moreover, in its current form, a catheter mounted IABP advanced retrograde from the femoral artery into the descending aorta requires the patient to remain supine for the duration of therapy. Consequently, patients cannot be ambulatory (or be discharged from the hospital). These limitations prevent the IABP from being used as an extended therapy for heart failure and instead are used in short term settings, such as in patients awaiting transplant and in patients undergoing coronary artery bypass surgery.

Several newer devices provide chronic counterpulsation but require invasive surgical implant procedures. These devices have been developed and introduced clinically (e.g., Symphony by Abiomed, CardioVAD by LVAD Technologies, and C-Pulse by Sunshine Medical), given the demonstrated hemodynamic and metabolic benefits of counterpulsation therapy. The Symphony counterpulsation device demonstrated hemodynamic efficacy in in-vivo animal studies, but clinical studies in Canada were discontinued. CardioVAD and C-Pulse devices reported increased cardiac output and end-organ perfusion as well as a significant decrease in NYHA functional class, indicating clinical improvement. However, the CardioVAD and C-Pulse have not achieved clinical acceptance due to the need to perform a full thoracotomy or sternotomy for device implant. The presence of previous heart surgeries thus limits the use of these devices. Furthermore, placement of either device may complicate further therapies such as LVAD or heart transplantation. Nevertheless, these clinical trials demonstrated the hemodynamic and clinical benefit of chronic counterpulsation therapy in patients with heart failure. The present Assignee/Applicant (NuPulseCV, Inc.) has developed a counterpulsation therapy system with lower device and hospitalization costs and a lower adverse event burden than LVAD therapies, and was the first chronic circulatory support device approved for a feasibility trial by the U.S. Food and Drug Administration (FDA) for NYHA Class III and IV heart failure patients without requirement for transplant listing (i.e., an all comers trial). Devices were successfully implanted in over 50 patients in the U.S. for up to 361 days with n=15 discharged out from the hospital. These devices demonstrated improvements in NYHA functional class, and statistically significant improvements in cardiac index (39%), cardiac power index (35%), and ejection fraction (48%) over baseline heart failure values. While less invasive than current LVAD therapies, these systems still required a surgeon, a surgical operating room, administration of general anesthesia, and approximately four hours. Thus, there is a significant unmet clinical need for a long-term mechanical circulatory support device that is less invasive, cheaper, non-obligatory, and/or carries a lower adverse event burden for NYHA Class III and IV heart failure patients.

The present technology offers a long-term or chronic counterpulsation therapy for heart failure patients that can be implanted using minimally invasive intravascular procedures. For example, the present technology includes intravascular ventricular assist devices that provide partial circulatory support, can be implanted minimally invasively without entering the chest, and generally do not require cardiopulmonary bypass or administration of blood products. In particular, the present technology includes an intravascular IABP delivery technique to further reduce the invasiveness of implantation and to enable cardiologists and other procedure-focused physicians to implant the device in a catheterization laboratory using standard minimally invasive techniques instead of extensive surgery. The intravascular implantation procedure does not require general anesthesia and can be accomplished in approximately 2 hours or less. The intravascular implantation procedure and associated devices and systems are anticipated to further lower surgical and hospitalization costs, as well as adverse events compared to the current IABP implant procedures and devices. Moreover, the devices and systems described herein are designed to provide long-term or chronic therapy to patients (e.g., greater than about six months).

Select Embodiments of Chronic Intravascular Circulatory Support Systems

FIG. 1 illustrates a circulatory support and/or intravascular ventricular assist system 100 ("system 100") configured in accordance with select embodiments of the present technology. The system 100 can include an expandable member 110 implantable in an aorta of a patient suffering from heart failure. The system 100 can further include a first driveline 120 (also referred to as an "internal driveline"), an arterial interface device or stopper device 130, a second driveline 140, a skin interface device 190, a drive unit 150, and sensors 160. When implanted, the system 100 can provide counterpulsation therapy to a patient suffering from heart failure.

The expandable member 110 can be a balloon or other element that can change size and/or shape in response to being filled with a gas or liquid. For example, in some embodiments the expandable member 110 is a balloon composed of a biocompatible, non-thrombogenic elastomeric material (e.g., Biospan®-S). The expandable member 110 can also be made of other suitable materials. The expandable member 110 is able to be transitioned between at least a first state in which it is generally deflated and a second state in which it is generally inflated. The expandable member 110 has a first volume when in the first (e.g., deflated) state and a second volume that is greater than the first volume when in the second (e.g., inflated) state. Accordingly, the expandable member 110 can provide counterpulsation therapy by repeatedly transitioning between the first state and the second state. To transition the expandable member 110 between the first state and the second state, the drive unit 150 can direct a fluid (gas or liquid, e.g., air) into an internal volume of the expandable member 110 via the first driveline 120 and the second driveline 140, as described in greater detail below. The expandable member 110 can also be sized and/or shaped to reduce and/or prevent the expandable member 110 from blocking arteries branching from the aorta, such as the renal arteries. Additional details of the expandable member 110 are described below with respect to FIGS. 3A-3C. In some embodiments, the expandable member 110 may also have certain features generally similar to those described in U.S. Pat. Nos. 8,066,628, 8,323,174, and 8,326,421, the disclosures of which are incorporated by reference herein in their entireties. In some embodiments, the expandable member 110 includes an expandable end effector other than or in addition to a balloon.

The first driveline 120 is an elongated structure having a lumen extending therethrough for delivering inflation gases to the expandable member 110. The first driveline 120 is able to be positioned at least partially within the patient's vasculature (e.g., between the aorta and an axillary or subclavian artery). After the system 100 is implanted, the first driveline 120 can have a first end portion (e.g., a distal end portion) coupled to the expandable member 110 and positioned within the patient's vasculature (e.g., within a descending aorta) and a second end portion (e.g., a proximal end portion) coupled to the second driveline 140 and positioned external to the patient's vasculature. The first driveline 120 can exit the patient's vasculature at an arteriotomy in, for example, an axillary artery, a subclavian artery, or another suitable blood vessel.

The second driveline 140 can also be an elongated structure having a lumen extending therethrough. The second driveline 140 is able to be positioned at least partially subcutaneously but external to the patient's vasculature. After the system 100 is implanted, the second driveline has a first end portion (e.g., a distal end portion) coupled to the first driveline 120 and a second end portion (e.g., a proximal end portion) coupled to the skin interface device 190. The first driveline 120 and the second driveline 140 can be made of the same or different materials, and can have the same or different dimensions (e.g., length, outer diameter, inner diameter, etc.). In some embodiments, the second driveline 140 may include an absorptive feature for reducing longitudinal strain that could otherwise be transferred to the first driveline 120 when the patient moves. For example, in some embodiments the absorptive feature is a curved region (e.g., an "S" shaped or other serpentine curve) that can compress in response longitudinal forces, thereby reducing and/or preventing the longitudinal forces from being transferred to the intravascular portions of the system 100 (e.g., the first driveline 120 and/or the expandable member 110).

The first driveline 120 can be coupled to the second driveline 140 using any suitable technique. In some embodiments, the first driveline 120 is inserted at least partially into the second driveline 140 (or vice versa) and secured thereto using a compression ring. In some embodiments, the first driveline 120 is sutured, glued, stitched, or otherwise secured to the second driveline 140. In some embodiments, the first driveline 120 is attached to the second driveline 140 via a combination of the foregoing techniques and/or via other suitable attachment techniques. Regardless of the connection mechanism, when the first driveline 120 is coupled to the second driveline 140, the lumen of the first driveline 120 is fluidly connected to the lumen of the second driveline 140 such that gases that flow through the lumen of the second driveline 140 also flow through the lumen of the first driveline 120. Although described as first and second drivelines, in some embodiments the first driveline 120 and the second driveline 140 can be a single, integral component.

As noted above, the first driveline 120 can be coupled to the expandable member 110 to deliver inflation gases thereto. For example, the first end portion of the first driveline 120 can be connected to the expandable member 110 such that the lumen extending through the first driveline 120 is in fluid communication with an interior of the expandable member 110. Accordingly, gas flowing through the lumen of the first driveline 120 towards the expandable member 110 can flow into the expandable member 110, causing the expandable member 110 to transition from the first state to the second state (e.g., causing the expandable member 110 to inflate). The first driveline 120 can also receive gas from the expandable member 110 as the expandable member 110 transitions between the second state and the first state (e.g., as the expandable member 110 deflates). Additional details of the first driveline 120 are described with respect to FIGS. 4A and 4B.

The arterial interface device or stopper device 130 provides long-term (e.g., greater than about 3 months, greater than about 6 months, greater than about 12 months, etc.) hemostasis at an arteriotomy where the first driveline 120 exits the vasculature (e.g., at the subclavian or axillary artery). The stopper device 130 may include a plurality of anchoring elements that can be used to secure the stopper device 130 in a desired orientation or position. Additional details of the stopper device 130 are described in greater detail with respect to FIGS. 8A and 8B. In some embodiments, the stopper device 130 can include certain features generally similar to those described in U.S. Pat. No. 7,892,162, the disclosure of which is incorporated by reference herein in its entirety. For example, the stopper device 130 can include a suture ring (e.g., a polyester velour patch sutured to the artery to provide mechanical support), a graft (e.g., a polyester textile defining a lumen and sutured to the suture ring and artery to provider arterial access), and a stopper element (e.g., a silicone plug inserted into the lumen of the graft to provide hemostasis having a lumen that receives the first driveline 120).

The skin interface device 190 is a transcutaneous device that enables the external drive unit 150 to drive operation of the implanted expandable member 110. For example, in some embodiments the skin interface device 190 provides a stable and/or secure exit site for the second driveline 140, enabling connection of the second driveline 140 directly to the drive unit 150. In other embodiments, the second driveline 140 can be coupled to an internal facing portion of the skin interface device 190, and the drive unit 150 can be coupled to an external facing portion of the skin interface device 190 (e.g., via a hose, conduit, or other tube 192). In such embodiments, the skin interface device 190 can direct gases received from the drive unit 150 (e.g., via the tube 192) to the second driveline 140 for delivery to the expandable member 110. In some embodiments, the skin interface device 190 can be generally similar to the skin interface devices described in U.S. Pat. No. 10,137,230, the disclosure of which is incorporated by reference herein in its entirety.

The drive unit 150 can generate gas flow into and out of the expandable member 110 via the first driveline 120 and the second driveline 140. For example, the drive unit 150 can generate a positive pressure to accelerate gases into the expandable member 110 via the first driveline 120 and the second driveline 140, thereby inflating the expandable member 110. The drive unit 150 can also induce a negative pressure to withdraw gases from the expandable member 110 via the first driveline 120 and the second driveline 140, thereby deflating the expandable member 110. The drive unit 150 can induce gas flow into and out of the expandable member 110 through a number of different mechanisms. For example, the drive unit 150 can utilize a bellows, a blower, a compressor, an accelerator, or other similar features to direct gas flow into and out of the expandable member 110. In some embodiments, the drive unit 150 can control the volume of air being pushed into the expandable member 110 to avoid overinflating the expandable member 110. For example, in an embodiment utilizing a bellows to generate air flow, the volume of airflow generated by the bellows (e.g., the volume of the bellows) can be matched to an interior volume of the expandable member 110. In some embodiments, the drive unit 150 uses ambient air from the environment surrounding the drive unit 150 (e.g., "room air") to drive operation of the system 100. Without being bound by theory, using ambient air is expected to reduce the size, weight, and/or cost of the drive unit 150 relative to a drive unit that relies on an internal gas or fluid supply (e.g., helium tanks). For example, in some embodiments the drive unit 150 is about 2.2 kg or less. Accordingly, in some embodiments the drive unit is portable/ambulatory. In other embodiments, the drive unit 150 can be operably coupled to or otherwise include a gas or fluid supply, such as helium tanks (not shown). The driveline can be disconnected near the skin interface device 190 when the system 100 is not being actively used.

The sensors 160 can sense one or more physiological parameters related to the patient's native heart rhythm to synchronize operation of the system 100 with the cardiac cycle. In particular, the one or more sensed physiological parameters can be used to automatically synchronize operation of the drive unit 150 with the patient's native heart beat to ensure the expandable member 110 is being inflated and deflated at appropriate times during the cardiac cycle. In some embodiments, the sensors 160 can sense the one or more physiological parameters in real time. As illustrated in FIG. 1, the sensors 160 can be coupled to the skin interface device 190 via subcutaneous wires 162. The skin interface device 190 can relay the measurements received from the sensors to the drive unit 150 via a wired or wireless connection. In other embodiments, the sensors 160 can be wirelessly connected to the drive unit 150 and can transmit the sensed measurements directly to the drive unit 150 without using the skin interface device 190. The sensors 160 can be implanted sensors, external sensors, or both implanted and external sensors. For example, in some embodiments, the sensors 160 are implanted bipolar electrodes positioned at and/or proximate the heart or other appropriate tissue to determine, for example, when the left ventricle is contracting or relaxing.

The system 100 provides chronic support of heart function and blood flow, while still allowing the patient to remain ambulatory. Typical ventricular assist devices require femoral access for the driveline and/or connection to large, stationary external control units, and therefore confine the patient to a hospital bed in supine position for the duration of therapy. In contrast, the system 100 allows the patient to move about relatively unencumbered. Moreover, the therapy level provided by the system 100 can be adjusted to match patient need. For example, the volume displacement and support ratio (e.g., 1:1, 1:2, 1:3 support) provided by the expandable member 110 can be adjusted to vary the support provided. Without being bound by theory, gradually reducing the volume displacement over time can result in a controlled loading of the heart which in some instances may be beneficial for cardiac recovery. Furthermore, unlike conventional circulatory support systems, the system 100 can be turned off to, for example, assess the ability of the patient to handle cardiac demand without support before removing the system 100, or for another suitable reason. In some embodiments, for example, the expandable member 110 is designed to remain in the aorta in a deflated condition for a relatively prolonged duration (e.g., for 23 hours in a single day). This is in direct contrast to conventional devices, which often must be removed if turned off for more than about 15 minutes because reactivation could result in a shower of emboli that formed when in the inactive state.

Select Methods of Intravascularly Implanting a Chronic Circulatory Support System The present technology provides intravascular implant devices, systems, and methods. FIGS. 2A-2G illustrate various stages of an intravascular implant procedure in accordance with select embodiments of the present technology. The implant procedure is described with respect to implanting the system 100 of FIG. 1, although the implant method can also be used to implant other intravascular ventricular assist devices and/or other types of intravascular devices.

Figure 2A:
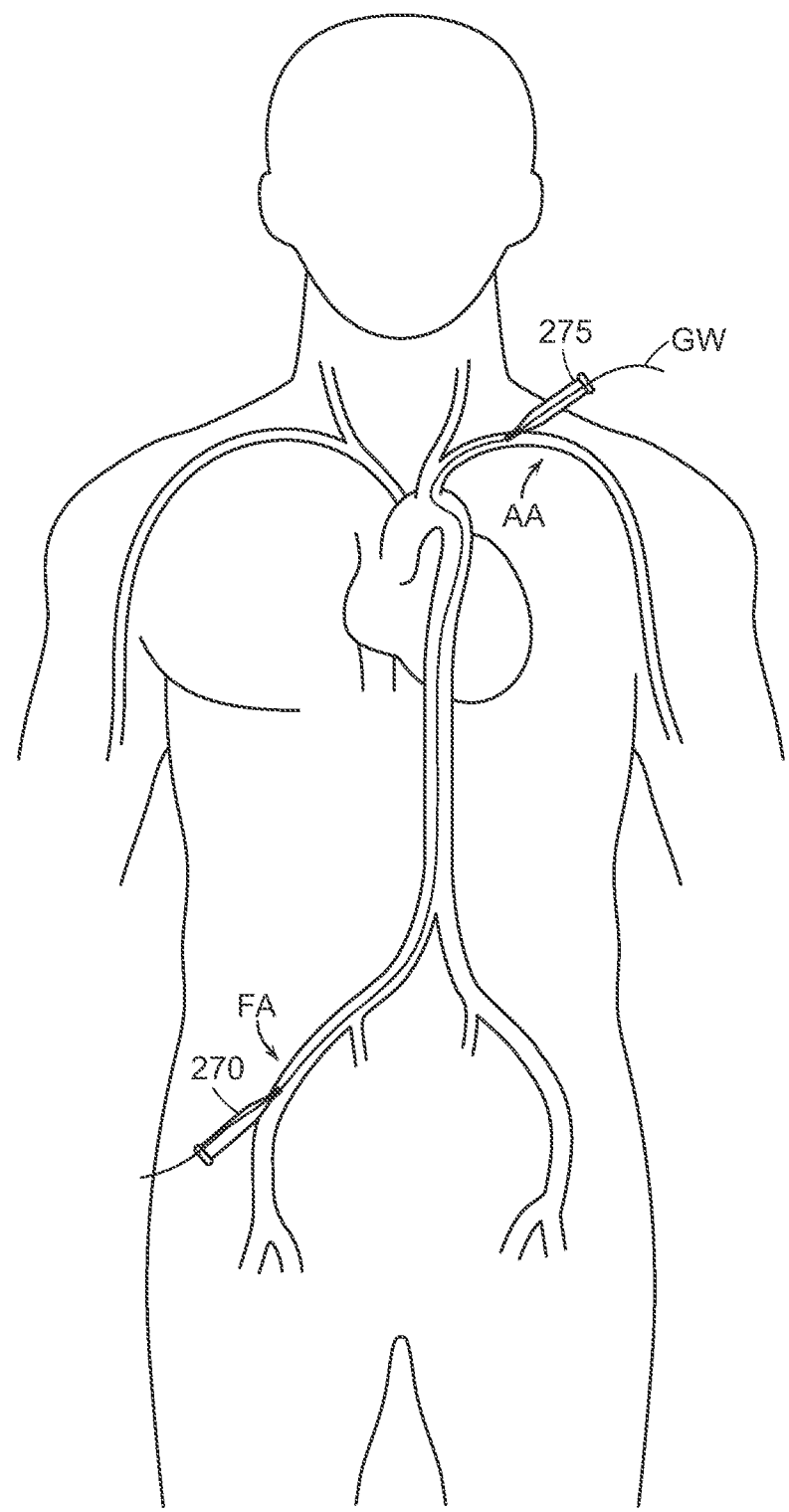
FIGS. 2A-2G illustrate various stages of a procedure for intravascularly implanting the circulatory support system illustrated in FIG. 1 in accordance with embodiments of the present technology.

The intravascular implant procedures of the present technology include establishing access to a patient's vasculature at two different locations. For example, FIG. 2A illustrates a first introducer sheath 270 inserted into a first blood vessel and a second introducer sheath 275 inserted into a second blood vessel. In the illustrated embodiment, the first blood vessel is a femoral artery FA and the second blood vessel is an axillary artery AA and/or a subclavian artery, although other blood vessels can be accessed and used. As one skilled in the art will appreciate, the subclavian artery is continuous with the axillary artery, with the transition between the two arteries typically defined at the lateral border of the first rib. Thus, while the following describes the intravascular implant procedures as using the axillary artery AA as the second blood vessel, the procedure can be performed in the same manner using the subclavian artery as the second blood vessel. Furthermore, although the illustrated embodiment shows the first introducer sheath 270 inserted in the right femoral artery, the first introducer sheath 270 can instead be inserted into the left femoral artery. Likewise, although the illustrated embodiment shows the second introducer sheath 275 inserted into the left axillary artery, the second introducer sheath 275 can instead be inserted into the right axillary artery. The practitioner can select the appropriate blood vessel based on for, example, patient anatomy, medical history, and other factors. The first introducer sheath 270 provides hemostatic, controlled access to the first blood vessel and the second introducer sheath 275 provides hemostatic, controlled access to the second blood vessel. For example, in some embodiments the first introducer sheath 270 includes a first hemostatic valve and the second introducer sheath 275 includes a second hemostatic valve.

To establish access to the target blood vessel (e.g., the axillary artery AA and/or the femoral artery FA), a practitioner can optionally first detect the target blood vessel using one or more imaging techniques (e.g., ultrasound, fluoroscopy). Following detection of the target blood vessel, the practitioner can make a micropuncture (e.g., needle puncture) in the target blood vessel using any suitable technique, such as the standard or modified Sedinger technique. With the needle inserted into the target blood vessel, the practitioner can insert a guidewire through the needle and into target blood vessel. The practitioner can remove the needle while leaving at least a portion of the guidewire in the blood vessel. In some embodiments, the blood vessel may subsequently be closed using conventional Perclose devices to minimize bleeding. In some embodiments, the practitioner may use multiple Perclose devices. The practitioner may also deploy a sheath (e.g., an 8 Fr sheath) or other dilator (e.g., a sidearm) over the guidewire to re-establish access to the blood vessel (e.g., if the blood vessel was previously closed with the guidewire remaining within). In some embodiments, the arteriotomy is progressively dilated using progressive dilators/sheaths (e.g., 10 Fr, 12 Fr, etc.). Once the target dilation is achieved, an introducer sheath can be inserted into the target blood vessel. In some embodiments, the introducer sheath is inserted into the blood vessel to further dilate the blood vessel towards the target dilation (e.g., it is inserted before the target dilation is achieved). Once the introducer sheath is in the blood vessel, the practitioner can then access the other target blood vessel (e.g., the axillary artery AA or the femoral artery FA) using the same or similar process.

The introducer sheath can be selected based on the target blood vessel. For example, in some embodiments the introducer sheath is a peel away sheath having a length of about 10 cm or greater. In other embodiments, the introducer sheath is a non-peel away sheath or other "longer" sheath having a length of about 30 cm or greater. For example, in patients having extreme subclavian artery tortuosity, using a non-peel away sheath at the axillary artery AA may simplify the process of establishing access to the axillary artery AA. In some embodiments, the introducer sheath can be expandable in the artery, such as a SoloPath™ sheath.

Returning to the illustrated embodiment, the first introducer sheath 270 at the femoral artery FA can have a diameter between about 12 Fr and about 20 Fr (e.g., about 16 Fr, about 18 Fr, etc.). The femoral artery FA can typically accommodate a larger diameter sheath, such as a 16 Fr sheath, than certain other locations of a patient's vasculature, including the axillary artery AA. Using a larger diameter sheath makes it easier to insert select components of, for example, the system 100, into the patient's vasculature. The second introducer sheath 275 can have a diameter between about 8 Fr to about 16 Fr (e.g., about 12.5 Fr, about 14 Fr, etc.).

Once access to the femoral artery FA and the axillary artery AA is established, a guidewire GW can be advanced through the patient's vasculature such that the guidewire GW extends between the femoral artery FA and the axillary artery AA, as illustrated in FIG. 2A. In particular, the guidewire GW can be externalized at the femoral artery FA via the first introducer sheath 270 and externalized at the axillary artery AA via the second introducer sheath 275, thereby establishing a "rail" between the first introducer sheath 270 and the second introducer sheath 275 in a technique referred to as "flossing" the patient. The guidewire GW can be any suitable guidewire long enough to extend between the first introducer sheath 270 and the second introducer sheath 275. For example, in some embodiments the guidewire GW has a length greater than about 200 cm (e.g., about 220 cm, about 240 cm, about 260 cm, etc.). The guidewire GW can have any suitable diameter (e.g., about 0.035 inches). In some embodiments, the guidewire GW is an exchange length angled wire (e.g., a Glide wire).

In some embodiments, the practitioner establishes the rail by inserting the guidewire GW through the second introducer sheath 275 and into the axillary artery AA. The practitioner then inserts a catheter (e.g., a 5 Fr MP-1 catheter, a JR4 catheter, etc.) through the first introducer sheath 270 and into the femoral artery. The practitioner can direct the catheter towards the axillary artery AA to capture the guidewire GW. The catheter can then be used to direct the guidewire GW from the axillary artery AA, into the distal aorta, and to the femoral artery FA (e.g., using a LAO 20° projection). The guidewire GW can then be externalized at the femoral artery FA via the second introducer sheath 275. If the guidewire GW does not penetrate the hemostasis valve on the first introducer sheath 270, the practitioner can insert a clamp into the hemostasis valve and attempt to once again advance the guidewire GW through the first introducer sheath 270. If the guidewire GW still does not penetrate the hemostasis valve, the guidewire can by clamped over the sheath and pulled while maintaining hemostasis using another suitable technique (e.g., manual compression over/above the access site). In such embodiments, a new introducer sheath can be advanced over the guidewire once externalized the GW is externalized at the femoral artery arteriotomy. Although the above technique describes inserting the guidewire GW through the second introducer sheath 275 and advancing it towards the first introducer sheath 270, in other embodiments the guidewire may alternatively be inserted through the first introducer sheath 270 and advanced towards the second introducer sheath 275 using a similar technique.

Figure 2B:
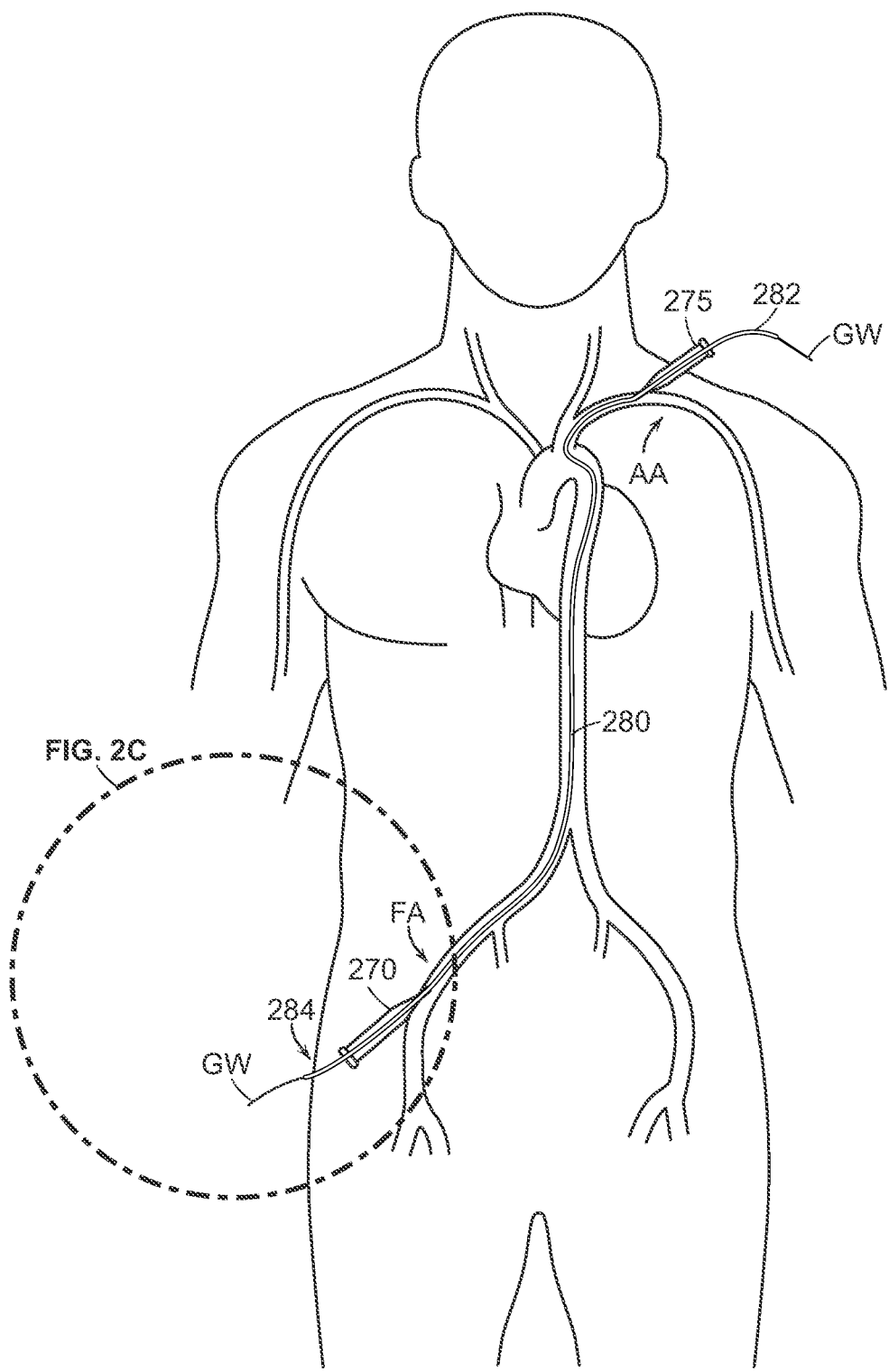
Figure 2C:
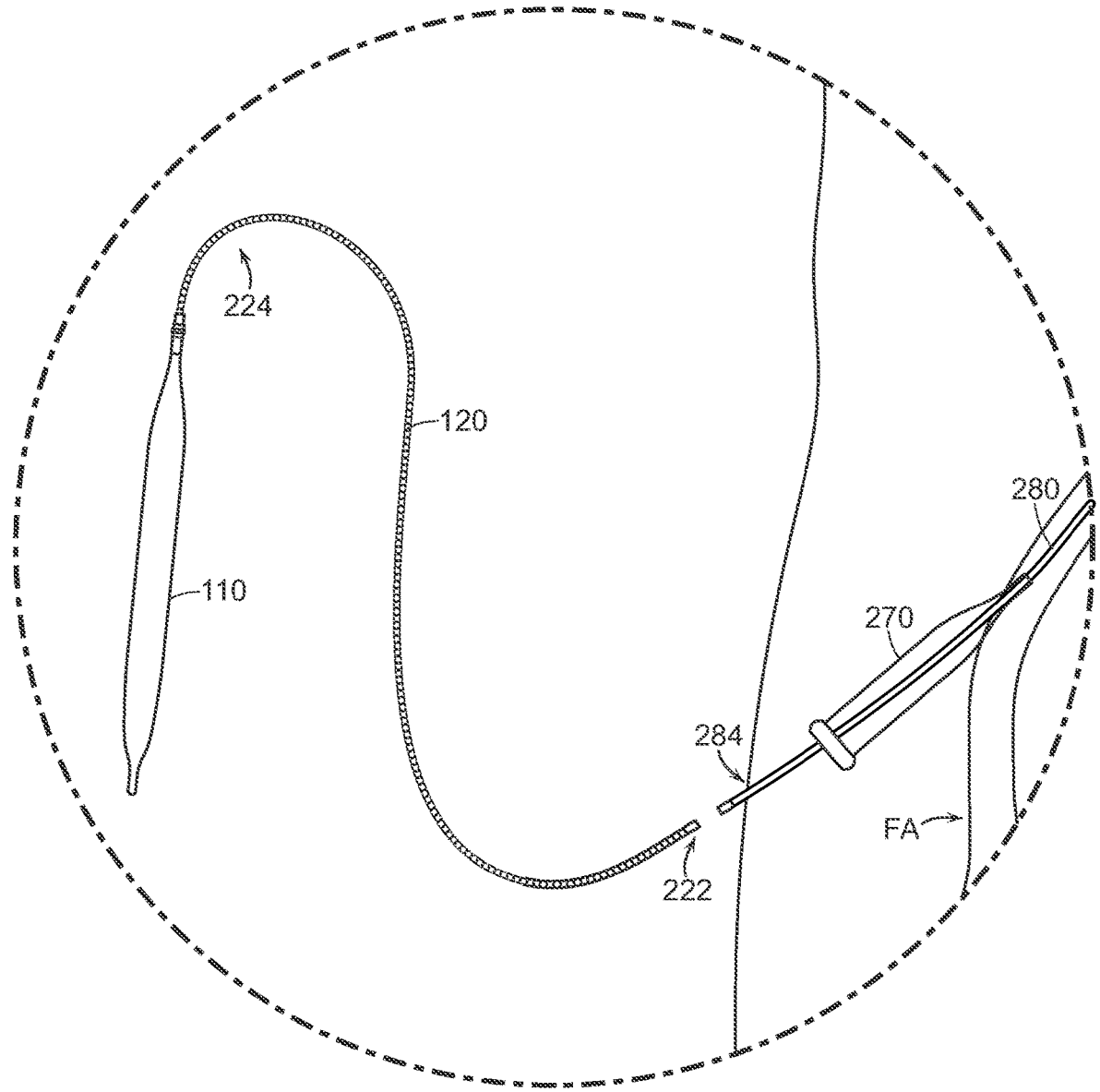

After the rail is established, an elongated delivery dilator 280 (also referred to as a "delivery tube," a "delivery shaft," a "delivery sheath," a "delivery catheter," or an "interceptor dilator") can be advanced over the guidewire GW to extend between the first introducer sheath 270 at the femoral artery FA and the second introducer sheath 275 at the axillary artery AA, as illustrated in FIG. 2B. For example, a practitioner can insert the elongated delivery dilator 280 into the patient's axillary artery AA via the second introducer sheath 275, advance the elongated delivery dilator 280 through a portion of the patient's vasculature, and externalize the elongated delivery dilator 280 through the first introducer sheath 270. As described in greater detail with respect to FIG. 5A, the elongated delivery dilator 280 can have an inwardly sloped or pointed end region to help guide it into the first introducer sheath 270 and penetrate the hemostatic valve therein in a retrograde direction. In some embodiments, the reverse operation is used to advance the elongated delivery dilator 280 (i.e., the elongated delivery dilator 280 is inserted through the first introducer sheath 270 and advanced towards the second introducer sheath 275). Following advancement of the elongated delivery dilator 280 through the patient's vasculature, a first portion 282 (e.g., a proximal end portion) of the elongated delivery dilator 280 is externally accessible proximate to the axillary artery AA and a second portion 284 (e.g., a distal end portion) of the elongated delivery dilator 280 is externally accessible proximate to the femoral artery FA. For example, FIG. 2C shows an enlarged view of the elongated delivery dilator 280 exiting the femoral artery FA via the first introducer sheath 270. Additional details of the elongated delivery dilator 280 are described in detail with respect to FIGS. 5A-5C. The guidewire GW can be removed once the elongated delivery dilator 280 is positioned as illustrated in FIG. 2B.

The externalized distal end portion 284 of the elongated delivery dilator 280 can be releasably connected to the first driveline 120. More specifically, the distal end portion 284 can be releasably connected to a first end region 222 of the first driveline 120, which also includes a second end region 224 connected to the expandable member 110. The elongated delivery dilator 280 can be secured to the first driveline 120 using a connector or other attachment mechanism. For example, as described in further detail with respect to FIGS. 4A-5C, the first end region 222 of the first driveline 120 can have a threaded female connection element, and the distal end portion 284 of the elongated delivery dilator 280 can have a threaded male connection element sized and shaped to interface with the threaded female connection element. Furthermore, as described with respect to FIGS. 5B and 5C, the distal end portion 284 of the elongated delivery dilator 280 can have a removable portion that covers the threaded male connection element until it is ready for connection to the driveline 120. Accordingly, in some embodiments the practitioner removes the removeable portion of the elongated delivery dilator 280 after the distal end portion 284 of the elongated delivery dilator 280 is externalized via the first introducer sheath 270 to expose the threaded male connection element. The practitioner then connects the elongated delivery dilator 280 to the first driveline 120 by screwing the threaded male connection element into the threaded female connection element on the first driveline 120.

Figure 2D:
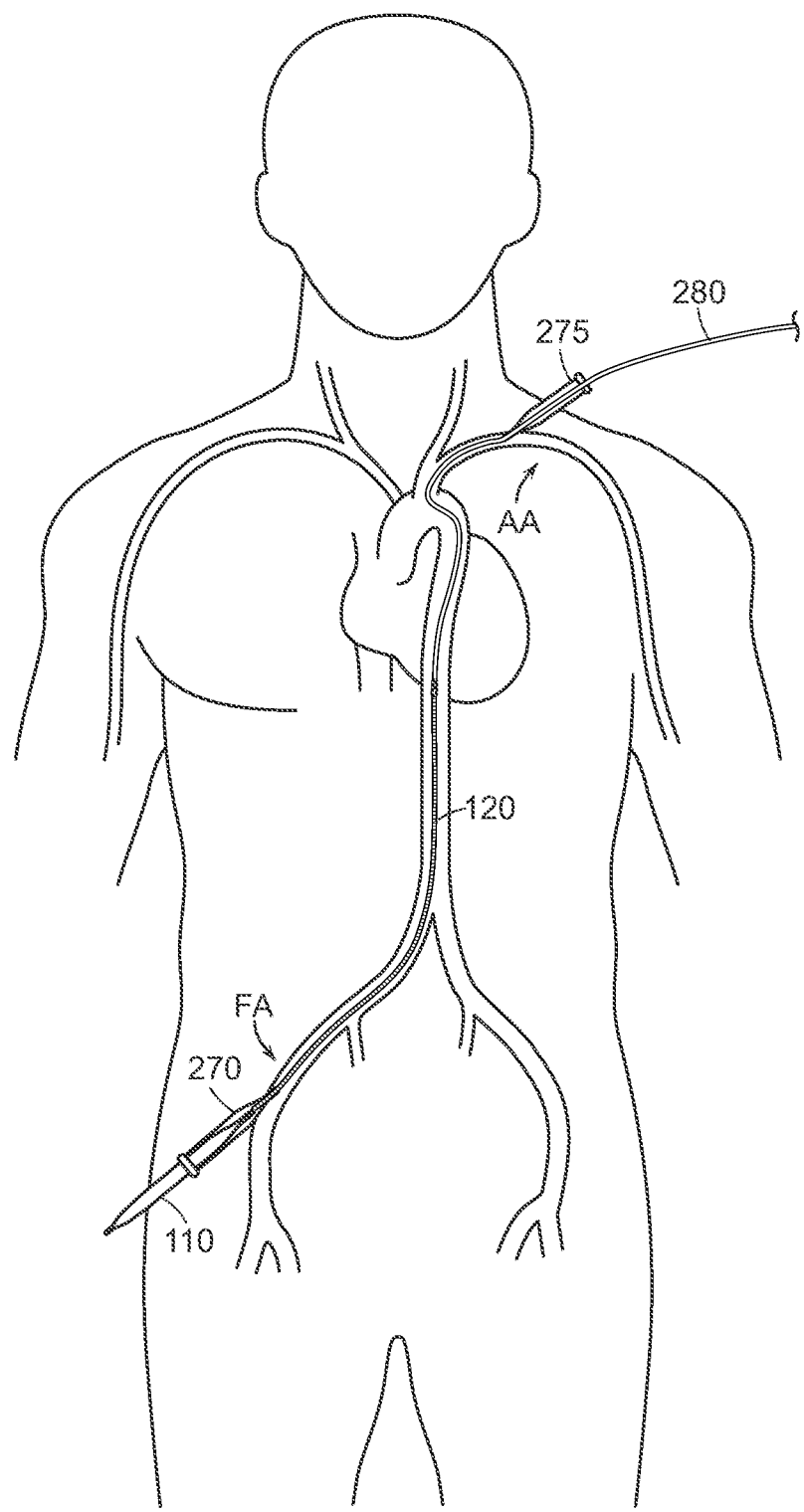

The first driveline 120 and the expandable member 110 move into the patient's vasculature through the first introducer sheath 270 by pulling on the proximal end portion 282 of the elongated delivery dilator 280. For example, once the elongated delivery dilator 280 is connected to the first driveline 120, the practitioner can pull the elongated delivery dilator 280 at the proximal end portion 282 externalized proximate the axillary artery AA. Because the elongated delivery dilator 280 is connected to the first driveline 120 at its distal end portion 284, the first driveline 120 and the expandable member 110 are pulled into the femoral artery FA via the first introducer sheath 270 as the elongated delivery dilator 280 is pulled out of the axillary artery AA via the second introducer sheath 275, as illustrated in FIG. 2D. The practitioner can continue to pull the elongated delivery dilator 280 out of the axillary artery AA, moving the expandable member 110 through the patient's vasculature in a direction opposite to blood flow. The practitioner can continue to pull the elongated delivery dilator 280 until the first driveline 120 is externalized proximate the axillary artery AA and/or the expandable member 110 is in a desired position (e.g., within the thoracic descending aorta). The positioning of the expandable member 110 can be confirmed via bony landmarks from CT and/or via contrast angiography using, for example, a 5F Omni™ Flush or pigtail catheter inserted via the first introducer sheath 270. In some embodiments, for example, the practitioner may wish to confirm that the expandable member 110 is positioned above, and thus does not block, the renal arteries.

In some embodiments, the first driveline 120 is long enough to extend between and through both the first introducer sheath 270 and the second introducer sheath 275 at the same time (e.g., about 200 cm or greater). This ensures that a portion of the first driveline 120 remains external to the patient while implanting the expandable member 110. Thus, if the first driveline 120 was inadvertently detached from the elongated delivery dilator 280 during the implant procedure, a portion of the first driveline 120 would still be external to the patient at the first introducer sheath 270 and/or the second introducer sheath 275, preventing the first driveline 120 and the expandable member 110 from being lost within the patient.

In some embodiments, the expandable member 110 is de-aired before pulling it into the femoral artery FA via the first introducer sheath 270. For example, a practitioner can attach a Y-connector to the proximal end portion 282 of the elongated delivery dilator 280. Because the lumen of the elongated delivery dilator 280 is in fluid communication with an interior of the expandable member 110 (via the first driveline 120), the practitioner can use a syringe or other pump element to remove any air from the expandable member 110. The practitioner can then close off the Y-connector (e.g., using a stopcock) to maintain a negative pressure in the expandable member 110, the first driveline 120, and the elongated delivery dilator 280. Without being bound by theory, de-airing the expandable member 110 is expected to reduce and/or minimize the profile of the expandable member 110, making it easier to pull through the first introducer sheath 270 and into the patient's vasculature.

In some embodiments, the expandable member 110 is folded, twisted, or otherwise placed in a delivery state with a decreased cross-sectional area before or while being pulled into the femoral artery FA via the first introducer sheath 270. For example, the expandable member 110 can be pulled through a funnel assembly or other folding tube to decrease one or more dimensions of the expandable member 110. Exemplary funnel assemblies and folding tubes are described in detail below with respect to FIGS. 6A-7C. In some embodiments, the expandable member 110 can be manually folded or twisted in addition to, or in lieu of, using a funnel assembly or other folding tube. Reducing a dimension (e.g., a cross-sectional dimension, an outer diameter, etc.) of the expandable member 110 is expected to make it easier to pull the expandable member 110 through the first introducer sheath 270 and into the patient's vasculature. In some embodiments, the folding and/or twisting can be done in combination with the de-airing procedure described above. In other embodiments, the folding and/or twisting can be done in lieu of the de-airing procedure described above. In some embodiments, the folding procedure can be performed immediately before pulling the expandable member 110 into the vasculature. In other embodiments, the expandable member 110 can come pre-loaded in the funnel assembly/folding tube. In some embodiments, however, no folding device is used and the expandable member 110 is directly loaded/pulled into and through the first introducer sheath 270.

If the expandable member 110 needs to be repositioned or does not easily move once the expandable member 110 is inside the patient's vasculature, the practitioner can remove the stopcock from the Y-connector and insert a wire (e.g., a 0.035 inch Supra Core wire—not shown) into the expandable member 110 via the elongated delivery dilator 280 and the first driveline 120. The wire can provide a rail for movement. The practitioner may also insert a dilator sheath (e.g., a 12 Fr Check-Flo® sheath) over the wire and into the expandable member 110 to provide a reinforced rail for movement. Additionally or alternatively, the practitioner can advance a second wire (e.g., an angled glide stiff wire) external to, but alongside, the elongated delivery dilator 280 and/or the first driveline 120 to act as a "buddy wire." This second wire may be inserted through the same (e.g., the original) dissection in the axillary artery AA, or a new micropuncture or arteriotomy can be made. Yet another option for facilitating movement of the expandable member 110 within the patient's vasculature is for the practitioner to insert a snare or other feature into the femoral artery FA via the first introducer sheath 270. The snare or other feature can releasably grab the expandable member 110. The expandable member 110 can then be both pushed and pulled towards the desired positioned within the patient's vasculature.

Figure 2E:
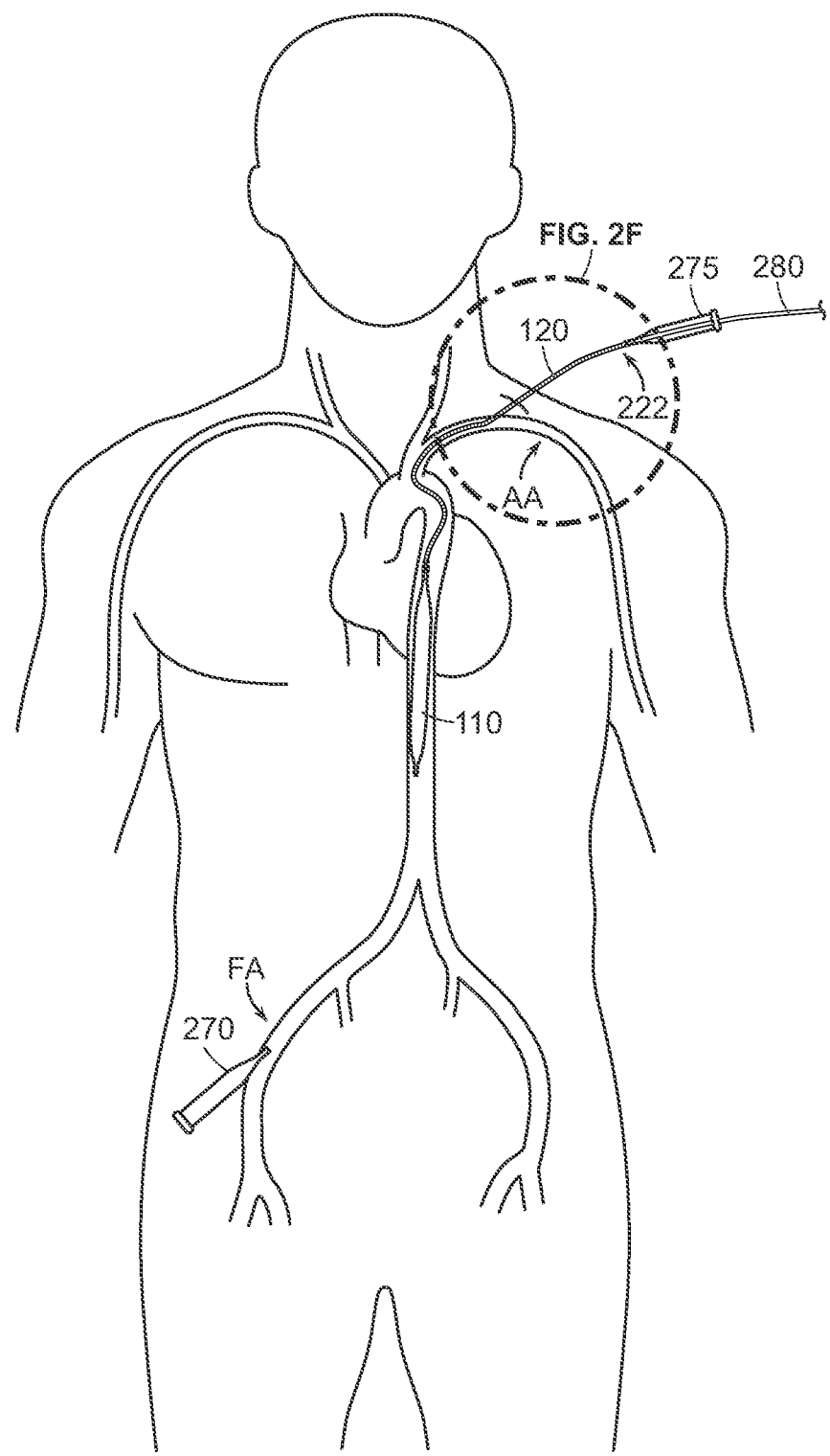

With the expandable member 110 within the patient's vasculature, the procedure continues by moving (e.g., pulling) the first driveline 120 with the expandable member 110 attached thereto through the patient's vasculature until the expandable member 110 is positioned at a target site. For example, as shown in FIG. 2E, the target site for the expandable member 110 can be within the descending thoracic aorta, at which point the first end region 222 of the first driveline 120 is also externalized proximate the axillary artery AA. In some embodiments, the first driveline 120 may exit via the second introducer sheath 275. For example, if the first driveline 120 has an outer diameter that is less than the diameter of the second introducer sheath 275 (e.g., the first driveline 120 is a 12.5 Fr driveline and the second introducer sheath 275 is a 14 Fr sheath), the first driveline 120 will exit the axillary artery AA through the second introducer sheath 275. If, however, the first driveline 120 has a greater diameter than the diameter of the second introducer sheath 275 (e.g., the first driveline 120 is a 12.6 Fr driveline and the second introducer sheath 275 is a 12.5 Fr sheath), the second introducer sheath 275 will be withdrawn from the axillary artery AA along with the first driveline 120, as shown in FIG. 2E. In some embodiments, the outer diameter of the driveline may be tapered or otherwise sloped such that the first end region 222 has a smaller outer diameter than the second end region 224. In such embodiments, the first end region 222 may fit through the second introducer sheath 275 while the second end region 224 cannot fit through the second introducer sheath 275. Once the first driveline 120 exits the patient's vasculature at the axillary artery AA, the elongated delivery dilator 280 can be disconnected from the first driveline 120 (e.g., by unscrewing the male connection element from the female connection element). Likewise, the second introducer sheath 275 can be removed, regardless of whether it remained in the axillary artery AA when the first driveline 120 was pulled out of the axillary artery AA.

Figure 2F:
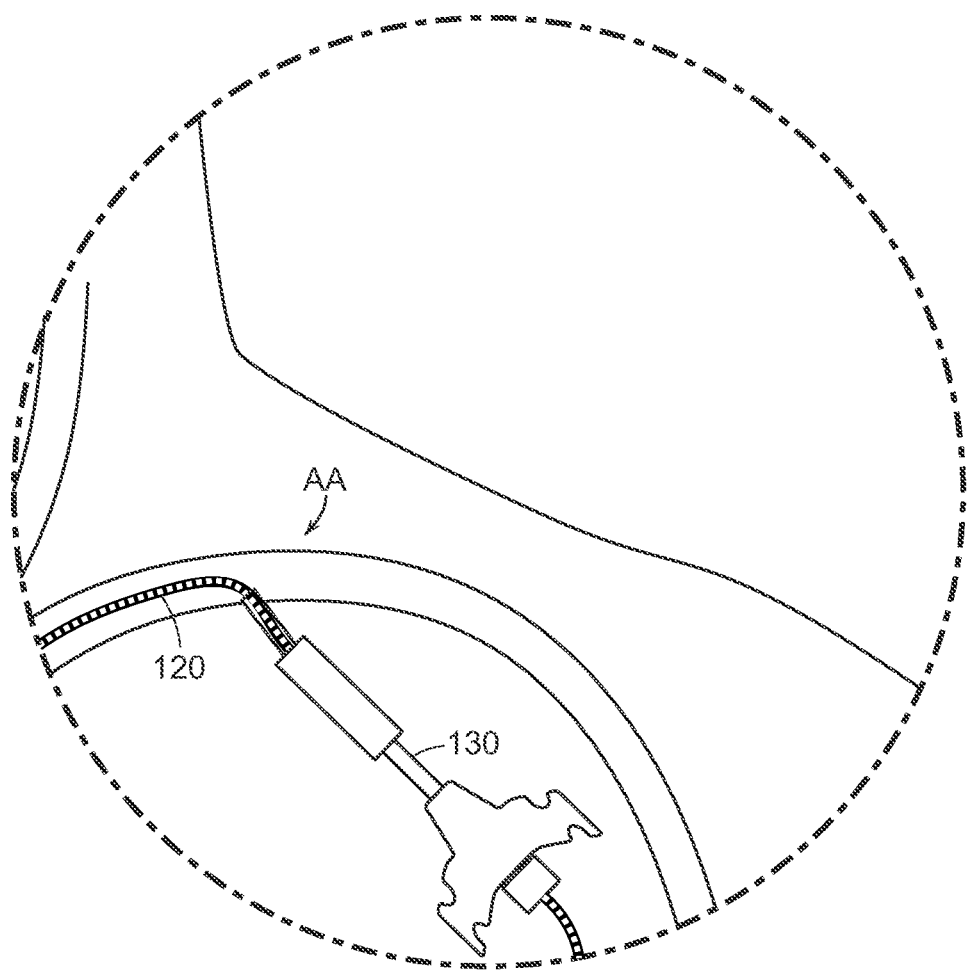

The practitioner can insert an arterial interface device (e.g., the stopper device 130) over the first driveline 120 to re-establish hemostasis at the axillary artery AA, as illustrated in FIG. 2F. At least a portion of the stopper device 130 can extend into the axillary artery AA to provide hemostasis. The practitioner can secure the stopper device 130 in place for long-term or permanent implantation using various suitable anchoring techniques or mechanisms. For example, the stopper device 130 may include an anchoring mechanism that provides stability near the arteriotomy site. As described below with respect to FIGS. 8A and 8B, the anchoring mechanism can be an expandable member, biocompatible glue, sutures, other suitable elements, or combinations thereof. In some embodiments, the stopper device 130 is an implantable stopper and is positioned subcutaneously. Accordingly, the stopper device 130 can remain in the patient to provide hemostasis at the axillary artery AA for the duration of the therapy.

In other embodiments, the practitioner may re-establish hemostasis at the axillary artery AA using other suitable techniques. For example, the practitioner may insert an angled guide wire into the femoral artery and advance a catheter (e.g., a JR4 catheter, an RDC catheter, etc.) over the guidewire and into the femoral artery FA. The catheter can be advanced through the patient's vasculature to the second introducer sheath 275 and exchanged for wire (e.g., a 0.018 inch V18 wire). An appropriately sized (e.g., based on CT or ultrasound) subclavian balloon (e.g., a 0.035 inch balloon) can be advanced over the wire. The second introducer sheath 275 can then be removed while the subclavian balloon is inflated to prevent blood flow. Perclose ProGlide® sutures can be tightened over the first driveline 120 exiting the axillary artery AA and manual pressure maintained to provide hemostasis. If hemostasis is not initially achieved, the subclavian balloon can be inflated in the axillary artery AA and held with manual pressure (e.g., for 10 minutes). If hemostasis is still not achieved, the practitioner can re-advance the second introducer sheath 275 to the axillary artery AA, verify that the position of the second introducer sheath 275 is in the arteriotomy via contrast injection, inject biocompatible glue (e.g., Floseal®), and confirm hemostasis after manual pressure.

The practitioner can also remove the first introducer sheath 270 from the femoral artery FA using a suitable vascular closure device and/or technique. For example, in some embodiments a practitioner can remove the first introducer sheath 270 and achieve hemostasis using a MANTA® vasculature closure device or other similar device. If hemostasis is not initially achieved at the femoral artery FA, the practitioner can optionally apply manual pressure or use a balloon, stent, or other device to achieve hemostasis.

Figure 2G:
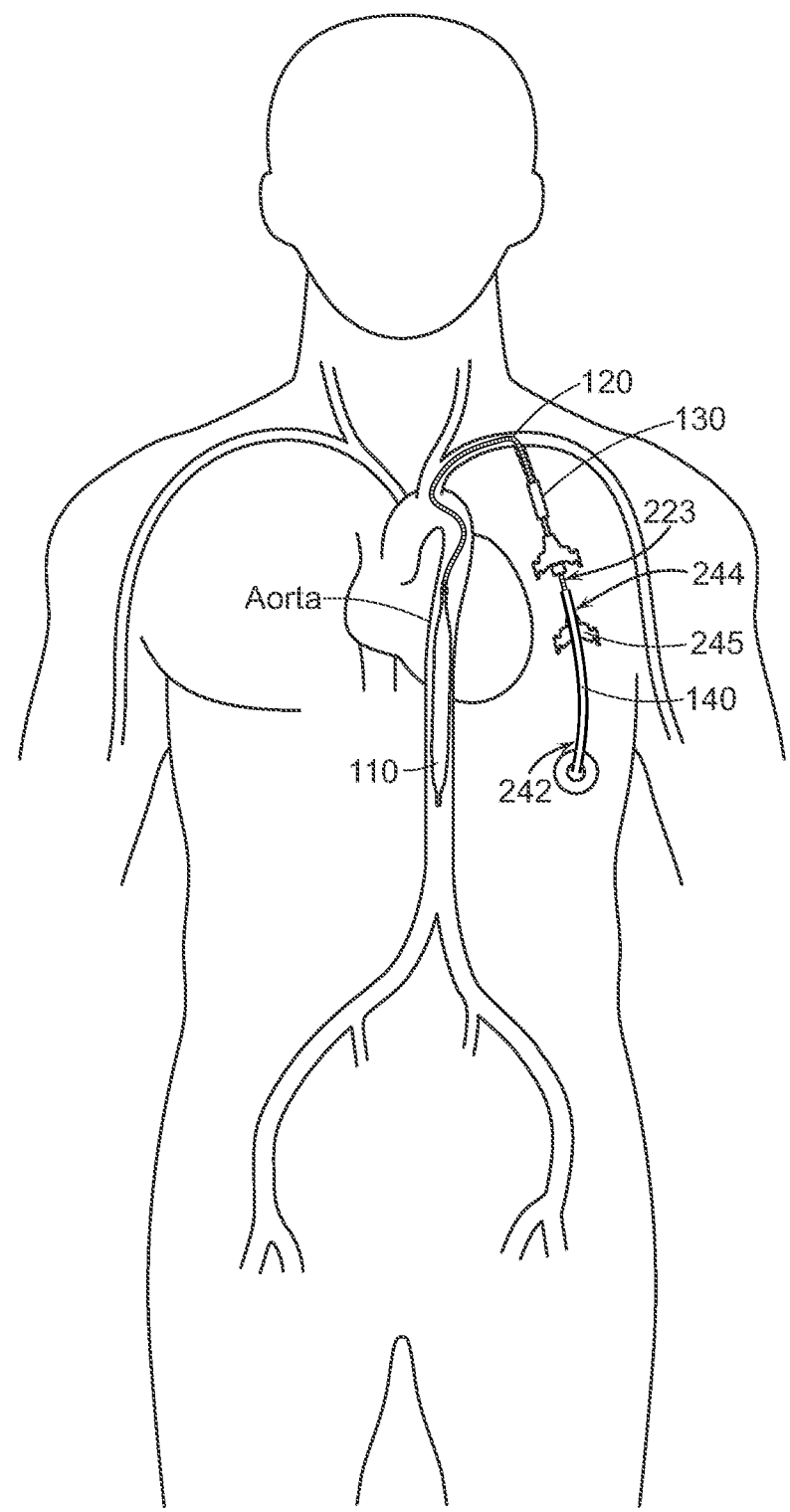

Turning to FIG. 2G, the practitioner can implant the second driveline 140 into the patient. For example, the practitioner can create a subcutaneous tunnel from the abdomen to the pectoral region, and advance the second driveline 140 through the tunnel from the abdomen to the pectoral region such that a first end region 242 of the second driveline 140 remains proximate the abdomen and a second end region 244 of the second driveline is proximate the stopper device 130.

As previously described, the first driveline 120 has a relatively long length to ensure that it extends between and through the femoral artery arteriotomy and the axillary artery arteriotomy during the implant procedure. Accordingly, a portion of the first driveline 120 may need to be removed so that it can be attached to the second driveline 140 and/or so that it fits within the patient. Accordingly, the practitioner can remove (e.g., cut, break off, detach, etc.) an excess length of the first end region 222 of the first driveline 120 extending out of the stopper device 130, thereby forming a "new" proximal end portion 223. The practitioner can then secure the proximal end portion 223 of the first driveline 120 to the second end region 244 of the second driveline 140 to form a pneumatic seal therebetween (e.g., sealed for up to 500 mmHg to prevent gas leakage), as shown in FIG. 2G. In some embodiments, the second end region 244 of the second driveline 140 has an inner diameter that is about equal to or slightly larger than an outer diameter of the proximal end portion 223 of the first driveline 120. For example, the second end region 244 of the second driveline 140 may have an inner diameter expandable to about 5 mm, and the proximal end portion 223 of the first driveline 120 may have an outer diameter of about 4.2 mm. The second end region 244 of the second driveline 140 can therefore be placed "over" at least a portion of the proximal end portion 223 of the first driveline 120. The second driveline 140 can then be secured to the first driveline 120 using a compression ring, sutures, or the like to provide the pneumatic seal between the first driveline 120 and the second driveline 140. Accordingly, in some embodiments the second driveline 140 can be referred to as an "overtube." Without being bound by theory, the relatively large inner diameter of the second driveline 140 is expected to enable faster shuttling of fluid (e.g., gas, such as air) to and from the expandable member 110 and facilitate connection of the second driveline 140 to the skin interface device 190.

Next, the first end region 242 of the second driveline 140 can optionally be trimmed to a suitable length and connected to the skin interface device 190 using barbs, mated threads, and/or other suitable connection features. In some embodiments, the second driveline 140 can further include anchoring features (not shown) for securing the second driveline 140 to tissue. For example, the second driveline 140 can include one or more wings or appendages 245 with a plurality of holes (not shown) for suturing the second driveline 140 to patient tissue. Accordingly, in some embodiments, the practitioner may anchor the second driveline 140 to tissue once the second driveline 140 is in the desired position. The practitioner can then connect the drive unit 150 to the skin interface device 190 to drive operation of the expandable member 110.

It is expected that the intravascular implant procedures described above with reference to FIGS. 2A-2G provide several benefits. For example, the intravascular approach for implanting intra-aortic blood pumps is less invasive than surgical methods. The intravascular procedures do not require a sternotomy or thoracotomy, nor do they require use of cardiopulmonary bypass or blood products. Rather, the procedures described herein can at least in some embodiments be completed using local anesthesia and in a cardiac catheterization lab by a cardiologist. This is expected to reduce the complexity, time, and cost associated with open surgical approaches for implanting circulatory support systems. The procedure is also expected to reduce hospitalization time and reduce rehospitalization and/or reoperation resulting from postoperative complications. In addition, the present intravascular procedures do not preclude the patient from receiving an LVAD and/or other cardiac support system if the disease progresses. This is in contrast with systems implanted via sternotomy or thoracotomy, since such operations may disturb the thoracic cavity and prevent further major surgery.

Moreover, the foregoing intravascular implant procedures also provide at least several advantages over other intravascular implant techniques for LVADs. For example, the foregoing technique enables the system 100 to be implanted in an orientation that permits long-term use of the system 100 and does not require the patient remain in a supine position for the duration of therapy. This is due at least in part to the orientation of the driveline 120, which extends in a cephalad direction (instead of caudally) from the expandable member 110 when implanted according to the foregoing intravascular implant procedure.

For at least the foregoing reasons, the intravascular procedures enable the use of circulatory support earlier in disease progression and in a larger class of patients relative to conventional procedures. For example, conventional circulatory support therapy (e.g., LVAD) was limited to advanced cases of heart failure due to the complexity and risk associated with implanting circulatory support systems. Using the present procedures, however, the reduced complexity, time, and cost, as well as the enhanced safety of intravascularly (rather than surgically) implanting circulatory support systems expands the class of patients who may be able to receive circulatory support systems. For example, the present technology may expand the availability of circulatory support therapy to all patients with NYHA class III or class IV heart failure, not just those with the most advanced cases.

As one skilled in the art will appreciate, various steps described above can be omitted and/or performed in alternative orders without deviating from the scope of the present technology. Likewise, the various steps and procedures described above can be performed using components other than those explicitly identified or described.

Select Methods of Removing and/or Replacing a Chronic Circulatory Support System An implanted circulatory support system, such as the iVAS system 100 described above with reference to FIGS. 1-2G, or a component thereof, may require removal or replacement for clinical reasons and/or reasons related to the device, such as myocardial recovery or device expiration. Accordingly, the present technology also provides methods for removing an implanted circulatory support system (e.g., the system 100) and/or portions thereof (e.g., the expandable member 110). For example, explant and/or replacement procedures described herein can remove the expandable member 110 from a location superior or cephalad to the implanted expandable member 110 (e.g., through the subclavian or axillary artery, as described below with respect to FIG. 2H), or from a location caudal to the implanted expandable member 110 (e.g., through the femoral artery, as described below with respect to FIG. 2I).

Figure 2H:
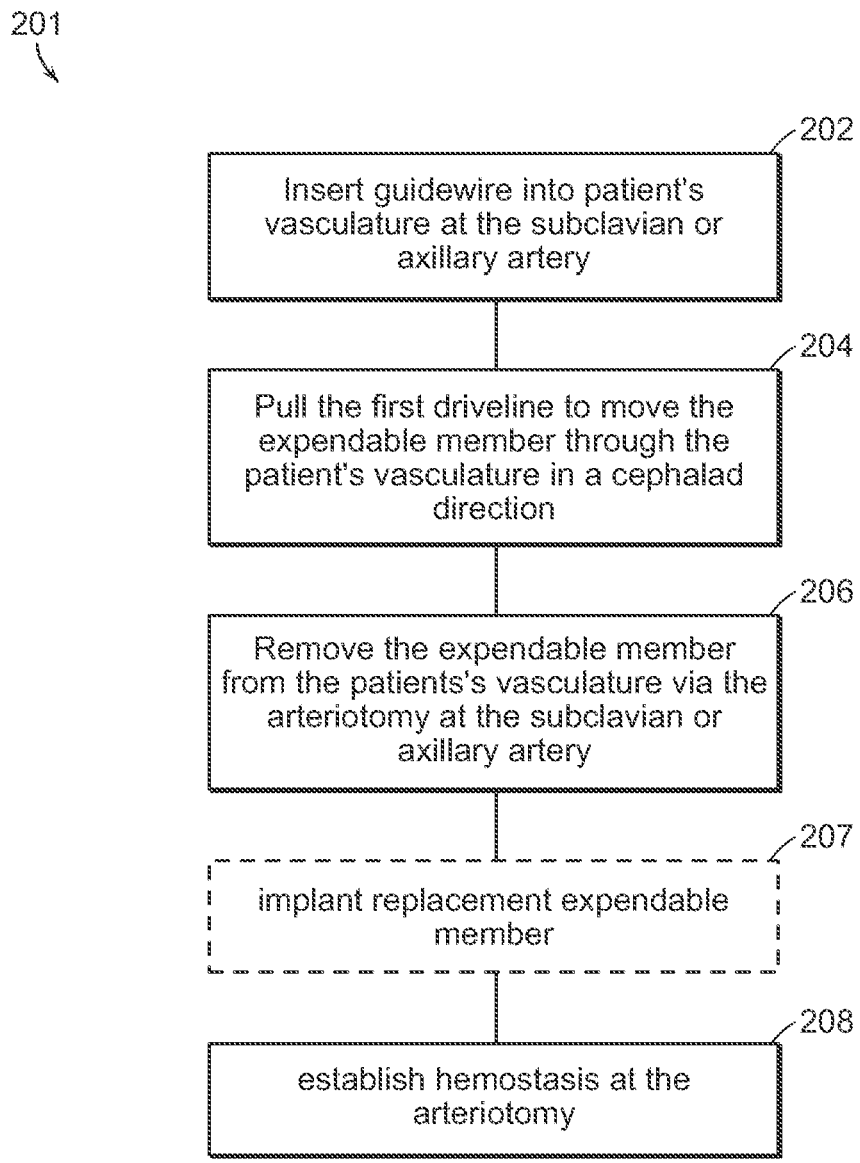
Figure 21:
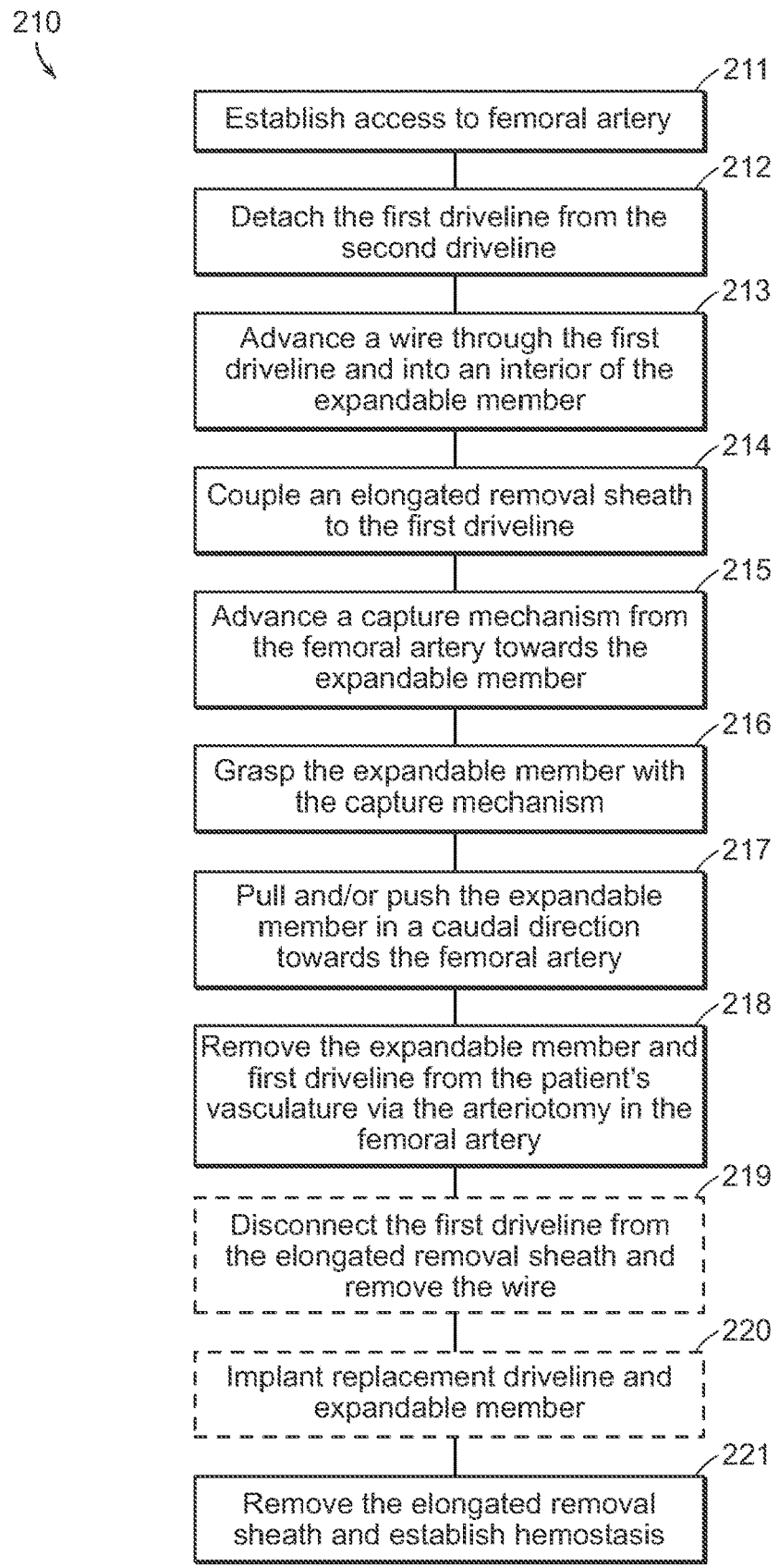

FIG. 2H is a flowchart illustrating an explant and/or replacement procedure 201 that removes the expandable member 110 through a subclavian or axillary artery in accordance with embodiments of the present technology. The explant procedure 201 will described with reference to the intravascular ventricular assist system 100 of FIG. 1 and various features of the associated delivery system illustrated in FIGS. 2A-2G, though the explant procedure 201 can be used to explant and/or replace other intravascular implants and/or using other delivery system features. The explant procedure 201 can begin by inserting a guidewire (e.g., similar to the guidewire GW shown in FIG. 2A) into the patient's vasculature at the subclavian or axillary artery AA (block 202). For example, the practitioner may insert the wire through a port in the stopper device 130 (e.g., through the second side port 839, described in further detail with respect to FIG. 8A) and into the patient's axillary artery AA. The wire remains external to the first driveline 120 (e.g., to the side of the first driveline 120) when inserted into the patient's vasculature. The procedure 201 can continue by pulling on the portion of the first driveline 120 that is external to the patient's vasculature to move the expandable member 110 through the patient's vasculature in a cephalad direction (block 204) and, eventually, through the arteriotomy in the axillary artery AA (block 206). In some embodiments, the expandable member 110 may be pulled out through the stopper device 130 while the stopper device 130 remains inserted into the axillary artery AA. In other embodiments, the stopper device 130 may be pulled out with the expandable member 110. In either case, the wire remains within the patient's vasculature after the first driveline 120 and the expandable member 110 are pulled out. In embodiments in which the stopper device 130 is also pulled out, the practitioner can re-achieve temporary or permanent hemostasis at the arteriotomy using over-the-wire arteriotomy closure techniques known to those skilled in the art (block 208).

The practitioner may optionally implant a second (e.g., new or replacement) expandable member (e.g., a balloon or other expandable member similar to the expandable member 110 described above) after the expandable member 110 is removed (block 207). If the practitioner wishes to implant a replacement expandable member, the practitioner can establish access, including wire access, to the femoral artery using the intravascular implant procedures described above with respect to FIGS. 2A-2D. In embodiments in which the stopper device 130 is pulled out of the axillary artery AA during removal of the expandable member 110, the practitioner can insert a new introducer sheath (e.g., similar to the second introducer sheath 275) into the axillary artery AA. The replacement expandable member can then be implanted using the intravascular implant procedure described above with respect to FIGS. 2A-2G. In embodiments in which the stopper device 130 remains inserted in the axillary artery AA following removal of the expandable member 110, the practitioner can remove the stopper device 130 from the axillary artery AA and insert a new introducer sheath (e.g., similar to the second introducer sheath 275) into the axillary artery AA. The replacement expandable member can then be implanted using the intravascular implant procedure described above with respect to FIGS. 2A-2G. In other embodiments, the stopper device 130, instead of the second introducer sheath 275, can provide access to the axillary artery AA, omitting the need for the second introducer sheath 275. The replacement expandable member can then be implanted using the intravascular implant procedure described above with respect to FIGS. 2A-2G, except using the stopper device 130 instead of the second introducer sheath 275.

FIG. 2I is a flowchart illustrating an explant and/or replacement procedure 210 that removes the expandable member 110 through a femoral artery in accordance with embodiments of the present technology. The explant procedure 210 will be described with reference to the intravascular ventricular assist system 100 of FIG. 1 and various features of the associated delivery system illustrated in FIGS. 2A-2G, though the explant procedure 210 can be used to explant and/or replace other intravascular implants and/or using other delivery system features. The procedure 210 can begin by establishing access to an artery caudal to the expandable member 110, such as the femoral artery FA (block 211). For example, the practitioner may insert a removal sheath into the femoral artery FA using a technique similar to that described above with respect to inserting the first introducer sheath 270 into the patient's femoral artery FA. In some embodiments, the removal sheath may be the same as, or at least generally similar to, the first introducer sheath 270. The practitioner can detach the first driveline 120 from the second driveline 140 to provide access to the interior lumen of the first driveline 120 (block 212). The practitioner can also optionally remove the stopper device 130. In some embodiments, however, the practitioner leaves the stopper device 130 in the axillary artery AA throughout the explant procedure 201.

The practitioner can advance a wire (e.g., similar to the guidewire GW shown in FIG. 2A) through the first driveline 120 and into an interior volume of the expandable member 110 (block 213). In some embodiments, the wire can include a snaring element that is advanced to the distal end region of the expandable member 110 (e.g., into the nipple 316, described in further detail with respect to FIG. 3B). The snaring element can be a ball, a hook, a "J" shape, or the like at the distal end portion of the wire. With the snaring element in the expandable member 110 and the wire extending from the snaring element and out of the first driveline 120, an elongated removal sheath (which can be the same as, or generally similar to, the elongated delivery dilator 280) can be coupled to the first driveline 120 external to the patient's axillary artery (block 214). The elongated removal sheath can be either directly or indirectly coupled to the first driveline 120. For example, in some embodiments an affixation device is inserted into the first driveline 120 over the wire with the snaring element before connecting the elongated removal sheath to the first driveline 120. The affixation device can have a fixation mechanism (e.g., a barb) to secure it to the first driveline 120 and a locking mechanism (e.g., a screw clasp, threads, mating surface, etc.) for securing it to the elongated removal sheath. In embodiments in which the stopper device 130 was removed, the elongated removal sheath may also be positioned inside a second sheath (e.g., generally similar to the second introducer sheath 275) before being advanced over the wire and coupled to the first driveline 120.

The practitioner can advance a capture mechanism through the removal sheath in the femoral artery and towards the expandable member 110 in the aorta (block 215). In some embodiments the capture mechanism is a catheter having one or more capture elements (e.g., a hook, a snare, graspers, etc.) that are sized and/or shaped to interact with the snaring element. The capture elements can optionally include one or more locking mechanisms for locking the capture elements once they have engaged the snaring element. Once the capture mechanism is proximate the expandable member 110 in the aorta, the practitioner can grasp the expandable member 110 using the one or more capture elements (e.g., by engaging the snaring element positioned within the expandable member 110) (block 216). The expandable member 110 can then be pulled towards the removal sheath in the femoral artery by pulling on the catheter and/or pushed towards the sheath in the femoral artery FA by pushing on the elongated removal sheath (block 217). As the expandable member 110 moves towards the removal sheath, the elongated removal sheath is pulled into the patient's vasculature at the axillary artery arteriotomy. In embodiments in which the stopper device 130 was removed and the elongated removal sheath was positioned within a second sheath, the second sheath can be advanced with the elongated removal sheath until it enters the axillary artery AA and provides hemostasis. If hemostasis is not initially achieved, a practitioner can apply manual pressure or insert a balloon to achieve hemostasis.

The practitioner can remove the expandable member 110 and the first driveline 120 from the patient's vasculature by pulling/pushing it through the removal sheath (block 218). In some embodiments, the expandable member 110 may not fit through the removal sheath, and the removal sheath will be pulled out of the femoral artery while removing the expandable member 110. In such cases, the practitioner can close the arteriotomy using standard techniques (e.g., using a MANTA® device), and/or apply manual pressure at the arteriotomy to minimize bleeding.

While the expandable member 110 and the first driveline 120 are pulled out of the removal sheath as a single unit, the elongated delivery dilator also advances through the removal sheath such that it extends between the patient's axillary artery and the patient's femoral artery, thus maintaining a pathway from the axillary artery to femoral artery. The first driveline 120 can optionally be disconnected from the elongated removal sheath, and the wire having the snaring feature can be removed from the elongated delivery dilator (block 219). A second wire (e.g., a 0.035" wire, an Amplatz stiff wire, a J wire, etc.) can optionally be passed through the elongated removal sheath from the femoral artery to the axillary artery. As a result, the ends of the wire and the elongated delivery dilator are outside the axillary and femoral arteries and enable access and control over the axillary and femoral arteriotomies. In embodiments in which the removal sheath came out while removing the expandable member 110 at the femoral artery arteriotomy, a second removal sheath (which can also be the same or generally similar to the first introducer sheath 270) can be pushed over the elongated removal sheath to achieve hemostasis at the femoral artery arteriotomy.

In some embodiments, the practitioner may implant a second (e.g., new or replacement) expandable member after the expandable member 110 is removed (block 219). To do so, the old driveline and expandable member are detached from the elongated removal sheath as described above, and a replacement driveline and expandable member (e.g., similar to the first driveline 120 and the expandable member 110 described above) can be attached in its place. The replacement expandable member can then be pulled into the vasculature by pulling on the elongated removal sheath proximate the axillary artery AA in a similar manner as the intravascular implant procedure described above with respect to FIGS. 2C-2G. In other embodiments, the practitioner may simply remove the elongated removal sheath and close the axillary artery arteriotomy and femoral artery arteriotomy using standard over-the-wire closure techniques (block 221).

These intravascular explant and replacement procedures and systems allow for removal and/or replacement of balloon pumps and/or other the intravascular devices using an intravascular approach, and therefore avoid major surgery. That is, removal of conventional circulatory support systems requires a second sternotomy procedure, which is associated with a marked increase in risk of adverse events and mortality. In contrast, the present technology provides minimally invasive intravascular procedures for removing and/or replacing the implanted device.

Select Components of Intravascular Delivery Systems and Intravascular Circulatory Support Systems FIGS. 3A-8B illustrate additional details of select components of the system 100 of FIG. 1 and the intravascular delivery system described above with respect to FIGS. 2A-2G. The components of the system 100 (i.e., an intraaortic ventricular assist device) described herein can be delivered via the intravascular delivery and/or replacement procedures described in FIGS. 2A-2I, or they may be delivered using other suitable implant procedures. The components of the delivery system described herein can be used to deliver and/or remove the system 100 to support blood flow and/or may be used to intravascularly deliver and/or remove other devices into or out of a patient's vasculature.

Figure 3A:
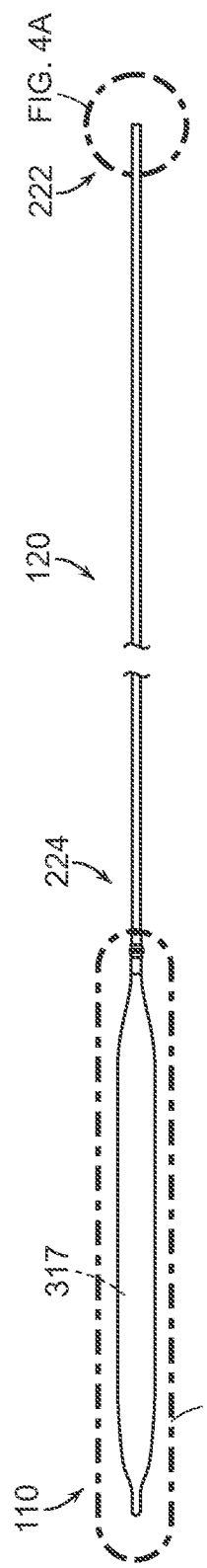
Figure 3B:
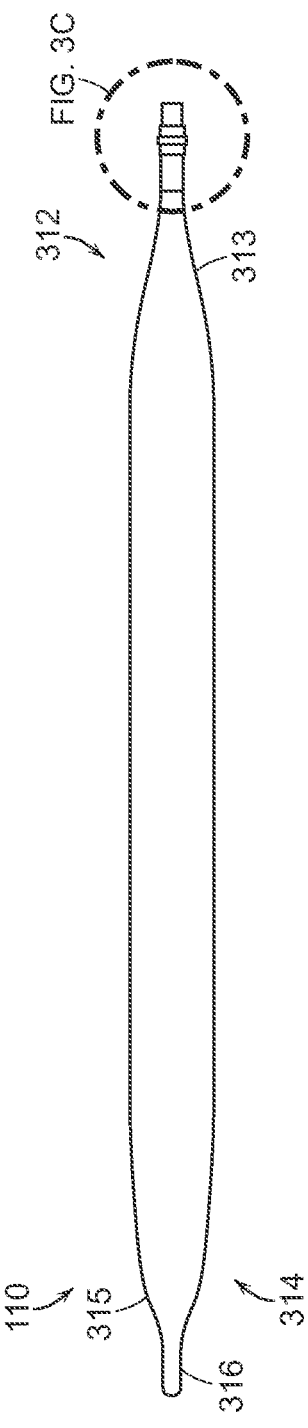

FIG. 3A is a side view of the expandable member 110 and the first driveline 120 configured in accordance with embodiments of the present technology. FIG. 3B is an enlarged side view of the expandable member 110 of FIG. 3A, and FIG. 3C is an enlarged side view of the connection between the expandable member 110 and the first driveline 120 configured in accordance with embodiments of the present technology. FIGS. 3A-3C illustrate the expandable member 110 in an inflated state (also referred to as a "first state" or an "expanded state") in which the expandable member 110 is at least partially filled with a fluid (e.g., gas, such as air). As shown FIG. 3A, the expandable member 110 is coupled to the second end region 224 of the first driveline 120, and a lumen extending through the first driveline 120 (described below with reference to FIGS. 4A-4B) is in fluid communication with an interior space 317 of the expandable member 110. Accordingly, the first driveline 120 can deliver gas (e.g., air) into and out of the expandable member 110 to drive inflation and deflation (expansion and compression) of the expandable member 110.

Referring now to FIG. 3B, the expandable member 110 can have a first (e.g., proximal) end portion 312 and a second (e.g., distal) end portion 314. The first end portion 312 can be connected to the first driveline 120, as described in greater detail with respect to FIG. 3C. The first end portion 312 can include an inwardly sloped or tapered neck 313 such that the cross-sectional diameter of the expandable member 110 at the sloped neck 313 decreases in a distal to proximal direction. In some embodiments, the first end portion 312 can have a greater material thickness relative to other portions of the expandable member 110. Without being bound by theory, the thicker material is expected to reduce kinking and stretching at the interface between the expandable member 110 and the first driveline 120.

The second end portion 314 can also include an inwardly sloped or tapered neck 315 such that the cross-sectional diameter of the expandable member 110 at the sloped neck 315 decreases in a proximal to distal direction. The sloped neck 315 is designed to be compatible with a narrowing of the aorta to avoid occluding branching vessels, such as the renal arteries, and thereby reduce the risk of renal ischemia when the expandable member 110 is implanted in a patient's aorta. The sloped neck 313 at the first end portion 312 and the sloped neck 315 at the distal end portion can also facilitate folding or twisting the expandable member 110 to reduce the dimensions of the expandable member 110 for implant and/or explant. The second end portion 314 can also optionally include a nipple or other engagement feature 316. In some embodiments, the nipple 316 is expected to facilitate snaring of the expandable member 110 during an intravascular explant procedure. For example, as described above, a snare or other capture feature can wrap around the nipple 316 to grasp the expandable member 110. In some embodiments, the nipple 316 can be sized and shape to receive a bulbous feature end of a wire, and a snare or other engagement mechanism can grasp around the bulbous feature in the nipple 316 to better engage the expandable member 110 for retrieval.

The expandable member 110 can transition between a deflated/unexpanded state (not shown) and the inflated/expanded state. For example, in some embodiments, the expandable member 110 is a balloon or other elastic structure. The balloon transitions from the deflated state to the inflated state when an interior of the balloon is filled with gas or fluid. The balloon transitions from the inflated state to the deflated state when the gas or fluid is withdrawn from the interior of the balloon. The expandable member 110 can also be another suitable structure that can transition between the unexpanded and expanded state. The expandable member 110 can be composed of any suitable biocompatible material. For example, the expandable member 110 can be composed of a biocompatible elastomer such as polyurethane (e.g., BioSpan® S). Without being bound by theory, it is expected that the expandable member 110 remains generally flat without folds or crevices when the expandable member 110 is in the deflated state. Unlike conventional intra-aortic balloon pumps, this enables the expandable member 110 to remain implanted in a patient even when the system 100 is turned off. Accordingly, in some embodiments the expandable member 110 is designed to remain in the patient even when the system is turned off. The expandable member 110 may remain in the patient when the system 100 is turned off for a prolonged period, such as more than one hour.

The expandable member 110 can be made in a variety of different sizes and/or shapes depending on, for example, patient anatomy and/or clinical need. In some embodiments, the expandable member 110 can have a displacement volume between about 20 ml and about 60 ml. For example, in some embodiments the displacement volume is about 50 ml. As used herein, displacement volume refers to the difference in volume between the inflated and deflated states. Accordingly, the displacement volume can be generally similar but not necessarily identical to the volume of the expandable member in the inflated state. The expandable member 110 can have a length between about 15 cm and about 30 cm. In some embodiments, for example, the expandable member 110 has a length greater than about 19 cm, such as about 20 cm or about 25 cm. Accordingly, in some embodiments the expandable member 110 is longer than conventional intraaortic balloon pumps. In particular, the sloped neck 315 at the second end portion 314 permits the expandable member 110 to have relatively greater lengths while keeping the risk of blocking the renal arteries low. As one skilled in the art will appreciate, the expandable member 110 can have other dimensions than those expressly recited herein to accommodate differing patient anatomy, such as for use in pediatric populations.

Referring to FIG. 3C, the first end portion 312 of the expandable member 110 is coupled to the second end region 224 of the first driveline 120. The first end portion 312 can include an engagement region 311 extending proximally from the sloped neck 313. The engagement region 311 can fit over a portion of the first driveline 120 (i.e., a portion of the first driveline 120 can be inserted at least partially into the engagement region 311). The engagement region 311 can be secured to the first driveline 120 using an attachment feature 318. The attachment feature 318 can be a compression ring or other suitable element that provides an airtight connection/pneumatic seal between the engagement region 311 and the first driveline 120, thereby preventing gases delivered to the interior space 317 of the expandable member 110 via the first driveline 120 from leaking out of the expandable member 110 into the external environment (e.g., into the patient's vasculature when the expandable member 110 is implanted).

Figure 4C:
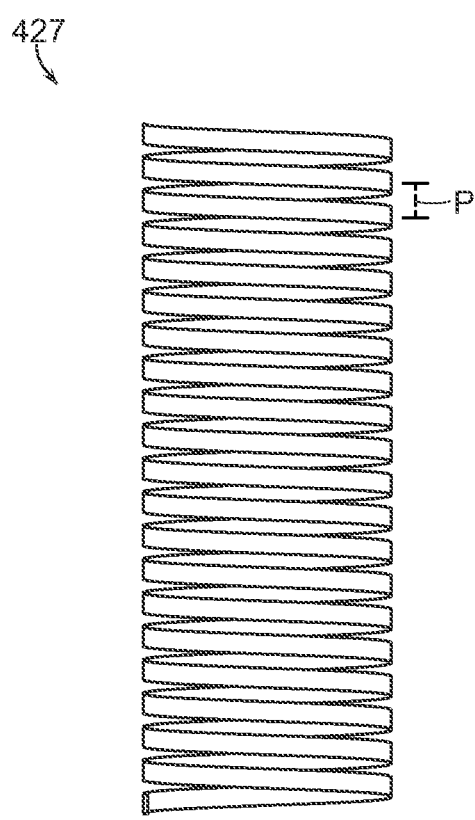
FIG. 4C is an enlarged side view of a kink-resistant element of the driveline shown in FIGS. 4A and 4B in accordance with embodiments of the present technology.

FIGS. 4A-4C illustrate various features of the first driveline 120 configured in accordance with embodiments of the present technology. FIGS. 4A and 4B are perspective and cross-sectional views, respectively, of the first driveline 120, and FIG. 4C is a side view of a kink-resistant element 427 of the first driveline 120. As shown in FIGS. 4A and 4B, the first driveline 120 can have a generally tubular wall 425 defining a lumen 421 extending therethrough. The generally tubular wall 425 can be gas impermeable to prevent gases from leaking out of the lumen 421 and into the patient's vasculature. In some embodiments, the generally tubular wall 425 can comprise a plurality of layers. In the illustrated embodiment, for example, the generally tubular wall 425 includes an inner membrane 426 and an outer membrane 428 concentrically enclosing the inner membrane 426. A coil or other helically wound kink-resistant element 427 (shown alone in FIG. 4C) can be disposed between and/or partially within the inner membrane 426 and the outer membrane 428. The inner membrane 426 and the outer membrane 428 can be composed of an at least partially flexible material. Furthermore, the outer membrane 428 can be composed of an antithrombogenic material, such as elastin-s, to reduce and/or prevent clot formation on the first driveline 120 when it is implanted in a patient's vasculature. The coil 427 can be composed of nitinol or another suitable kink-resistant material. In some embodiments, the coil 427 can have a pitch P less than about 1 mm (e.g., about 0.5 mm). Without being bound by theory, incorporation of the coil 427 into the tubular wall 425 provides several advantages, including, (1) providing added stability to the generally tubular wall 425, (2) reducing the required thickness of the generally tubular wall 425 to achieve a desired stability, and (3) reducing and/or preventing the first driveline 120 from kinking or collapsing. In some embodiments, the coil 427 only extends along a portion of the first driveline 120, dividing the first driveline into a "reinforced" and "unreinforced" section. In other embodiments, the coil 427 extends along the entire or approximately the entire length of the first driveline 120.

Figure 5C:
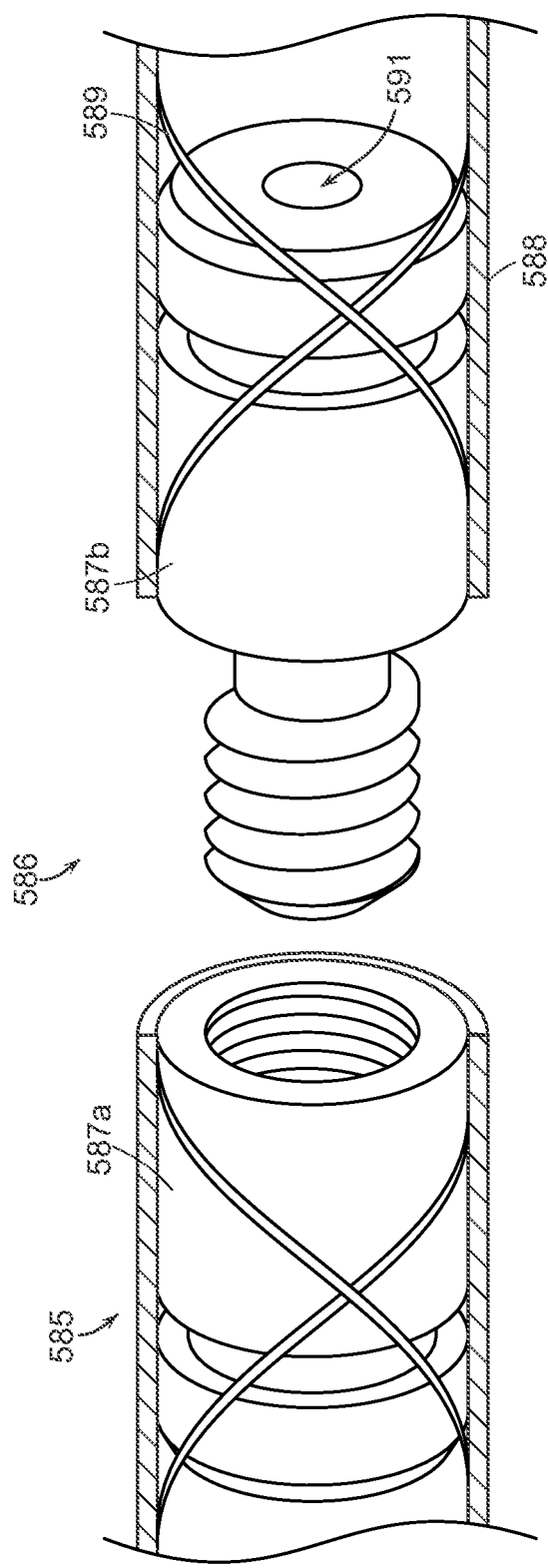

The first end region 222 of the first driveline 120 can also include a connection element 429 for connecting the first driveline 120 to the elongated delivery dilator 280 (FIGS. 5A-5C). Accordingly, the connection element 429 can also be referred to as the elongated delivery dilator connection element 429. The connection element 429 can be a threaded female connection element that is sized and shaped to receive a corresponding threaded male connection element on the elongated delivery dilator 280. In other embodiments, the connection element 429 can be a threaded male connection element that is sized and shaped to receive a corresponding threaded female connection element on the elongated delivery dilator 280. In yet other embodiments, the connection element 429 is another suitable fastening mechanism to secure the first driveline 120 to the elongated delivery dilator 280. In some embodiments, the connection element 429 includes an aperture 429a or other feature that permits air to flow through and/or around the connection element 429 and into the lumen 421. Thus, when the first driveline 120 is connected to the elongated delivery dilator 280 via the connection element 429, gas can flow through the elongated delivery dilator 280 and into the lumen 421 via the aperture 429a, and vice versa.

The first driveline 120 can have an outer diameter less than about 6 mm. For example, in some embodiments the outer diameter is about 4.2 mm. In other embodiments, the outer diameter is less than about 4.2 mm. In particular, the outer diameter of the first driveline 120 can be selected such that it fits through the first introducer sheath 270 and/or the second introducer sheath 275 during the intravascular implant procedures described herein. For example, in some embodiments the first driveline 120 has an outer diameter of 4.2 mm (e.g., 12.6 Fr), the first introducer sheath 270 is a 16 Fr sheath, and the second introducer sheath 275 is a 14 Fr sheath. In such embodiments, the first driveline 120 will fit through both the first introducer sheath 270 and the second introducer sheath 275. The outer diameter can also be small enough to fit within varying patient anatomy (e.g., larger drivelines can only be implanted in patients with axillary artery diameters above a certain threshold). The first driveline 120 can have an inner diameter (i.e., the diameter of the lumen 421, defined by the inner membrane 426) between about 2 mm and 5 mm. For example, in some embodiments the inner diameter is about 3.3 mm. In other embodiments the inner diameter is less than 3.3. mm.

The first driveline 120 has a relatively long length. For example, the first driveline 120 can be greater than about 200 cm (e.g., about 300 cm). As described above, having a relatively long length ensures that a portion of the first driveline 120 remains external to the patient during the implant procedure. If the first driveline 120 becomes disconnected from the elongated delivery dilator 280 during the implant procedure, the portion of the first driveline 120 that remains external to the patient can be used to retrieve the first driveline 120 and the expandable member 110 from the patient's vasculature. Because of the relatively long length, the first driveline 120 is generally cut before securing the first driveline 120 to the second driveline 140. For example, a portion of the first end region 222 can be removed, thereby removing the portion of the first driveline 120 having the connection element 429, which is no longer needed because the first driveline 120 is in position before cutting the first driveline 120.

In embodiments in which only a portion of the first driveline 120 is reinforced, the reinforced portion may have a first outer diameter that is greater than a second outer diameter of the unreinforced portion. For example, the reinforced portion may have an outer diameter of about 4.2 mm and the unreinforced portion may have an outer diameter of about 4 mm. In such embodiments, the reinforced portion can have a length greater than about 30 cm and the unreinforced portion can have a length greater than about 10 cm. In some embodiments, the reinforced portion includes the second end region 224 and the unreinforced portion includes the first end region 222. The transition between the first and second outer diameters can be tapered or otherwise gradual.

FIGS. 5A-5C are side, partial cross-sectional views of various features of the elongated delivery dilator 280 configured in accordance with embodiments of the present technology. As shown in FIG. 5A, the elongated delivery dilator 280 forms a generally tubular conduit, shaft, pipe, or the like having a lumen 592 extending therethrough. The lumen 592 is sized such that the elongated delivery dilator 280 can be advanced over a wire (e.g., a 0.035 inch wire). As previously described, the elongated delivery dilator 280 can include a first portion 282 (e.g., a proximal end portion) and a second portion 284 (e.g., a distal end portion). In some embodiments, the proximal end portion 282 can include a valve or port 853 (e.g., a check valve, a Luer lock, a sealable silicone port, etc.) for providing controlled access to the lumen 592. For example, a syringe, Y-connector, 3-way stopcock, or the like can be attached to the first driveline 120 at the valve 853 to de-air the expandable member 110 before pulling it into the patient's vasculature, as described previously with respect to FIG. 3D. In embodiments including the port 583, the port 583 remains external to the patient (e.g., at the axillary artery access site) throughout the implant procedure. The distal end portion 284 of the elongated delivery dilator 280 can be designed to penetrate a hemostatic valve in an introducer sheath (e.g., the first introducer sheath 270) when inserted into the introducer sheath in a retrograde direction. For example, in the illustrated embodiment the distal end portion 284 is at least partially pointed and/or inwardly sloped to help it penetrate a hemostatic valve.

A distalmost segment of the distal end portion 284 can include a removable portion 585 (e.g., a removable distal tip). The removable portion 585 can be secured to the elongated delivery dilator 280 at an attachment interface 586, described in detail below with reference to FIGS. 5B and 5C. During the intravascular implant procedures described herein, the removable portion 585 is removed from the elongated delivery dilator 280 after the distal end portion 284 is externalized at the first introducer sheath 270 (e.g., proximate to the femoral artery). The first driveline 120 is then connected to the elongated delivery dilator 280 at the attachment interface 586.

FIGS. 5B and 5C illustrate additional features of the elongated delivery dilator 280 proximate the attachment interface 586. More specifically, FIG. 5B illustrates the removable portion 585 connected to the elongated delivery dilator 280 at the attachment interface 586, and FIG. 5B illustrates the removable portion spaced apart (e.g., disconnected) from the elongated delivery dilator 280 at the attachment interface 586. Referring to FIGS. 5B and 5C together, the elongated delivery dilator 280 includes a first connection element 587a and a second connection element 587b proximate the attachment interface 586. The first connection element 587a and the second connection element 587b engage to releasably secure the removable portion 585 to the elongated delivery dilator 280. In the illustrated embodiment, the first connection element 587a is a threaded female connection element and the second connection element 587b is a threaded male connection element. In operation, the removable portion 585 can be releasably secured to the elongated delivery dilator 280 by screwing the threaded male connection element into the threaded female connection element. The removable portion 585 can be removed from the elongated delivery dilator 280 by unscrewing the threaded female connection element from the threaded male connection element. In other embodiments, the first connection element 587a is a threaded male connection element and the second connection element 587b is a threaded female connection element. Regardless, the first connection element 587a and the second connection element 587b can include apertures 591 extending therethrough to allow the elongated delivery dilator 280 to be advanced over a wire.

The first connection element 587a and the second connection element 587b may be composed of a generally inflexible material (e.g., stainless steel). Because the first connection element 587a and the second connection element 587b are composed of a generally inflexible material, the elongated delivery dilator 280 may not bend or flex at the attachment interface 586. Therefore, to ensure that the elongated delivery dilator 280 can be routed through various curves in the patient's vasculature despite the stiffness at the attachment interface 586, the first connection element 587a and the second connection element 587b can have a relatively short combined length when connected. For example, the first connection element 587a and the second connection element 587b can have a combined length less than about 2 cm and/or less than about 1 cm.

The second connection element 587b can also be used to connect the first driveline 120 to the elongated delivery dilator 280 (once the removable portion 585 is removed) by engaging the elongated delivery dilator connection element 429 on the first driveline 120. Accordingly, the second connection element 587b can also be referred to as the driveline connection element 587b. In embodiments in which the elongated delivery dilator connection element 429 on the first driveline 120 is a threaded male connection element, the second connection element 587b is a threaded female connection element. Likewise, in embodiments in which the elongated delivery dilator connection element 429 is a threaded female connection element, the second connection element 587b is a threaded male connection element. The aperture 591 on the second connection element 587b aligns with the aperture 429a on the elongated delivery dilator connection element 429 to place the elongated delivery dilator 280 in fluid connection with the lumen 421 of the first driveline 120. This permits gases to be withdrawn from the expandable member 110 and through the first driveline 120 and the elongated delivery dilator 280 during, for example, the de-airing procedure previously described.

Referring to FIGS. 5A-5C together, the elongated delivery dilator 280 can include an outer membrane 588. The outer membrane 588 is gas impermeable and can be composed of any suitable biocompatible and/or anti-thrombogenic material. For example, in some embodiments the outer membrane 588 is composed of elastin-S. In some embodiments, the elongated delivery dilator 280 also includes one or more reinforcement wires 589. In some embodiments, the reinforcement wires 589 are generally similar to the coil 427 in the first driveline 120. For example, the reinforcement wires 589 can be one or more helically wound nitinol coils that are generally kink-resistant. Although only shown proximate the attachment interface 586, the reinforcement wires 589 can extend along a full length or a substantial length of the elongated delivery dilator 280. In other embodiments, however, the reinforcement wires 589 are only located proximate the attachment interface 586 to provide added stability at the attachment interface 586.

The elongated delivery dilator 280 can have an outer diameter less than about 6 mm (excluding the port 583 in embodiments in which it is included). For example, in some embodiments the outer diameter is about 4.2 mm. In other embodiments, the outer diameter is less than about 4.2 mm.

In particular, the outer diameter of the elongated delivery dilator 280 can be selected such that it fits through the first introducer sheath 270 and/or the second introducer sheath 275 during the implant procedures described herein. For example, in some embodiments the elongated delivery dilator 280 has an outer diameter of 4.2 mm (e.g., 12.6 Fr), the first introducer sheath 270 is a 16 Fr sheath, and the second introducer sheath 275 is a 14 Fr sheath. Accordingly, elongated delivery dilator 280 will fit through both the first introducer sheath 270 and the second introducer sheath 275. The outer diameter can also small enough to permit the elongated delivery dilator 280 to fit within and through varying patient anatomy. In some embodiments, the elongated delivery dilator 280 has an outer diameter that is the same and/or about the same as the outer diameter of the first driveline 120. The elongated delivery dilator 280 also has a relatively long length. For example, the elongated delivery dilator 280 can have a length that is greater than about 200 cm (e.g., about 300 cm). As described above, having a relatively long length ensures that the elongated delivery dilator 280 can extend between the first introducer sheath 270 and the second introducer sheath 275.

Figures 6A, 6B:
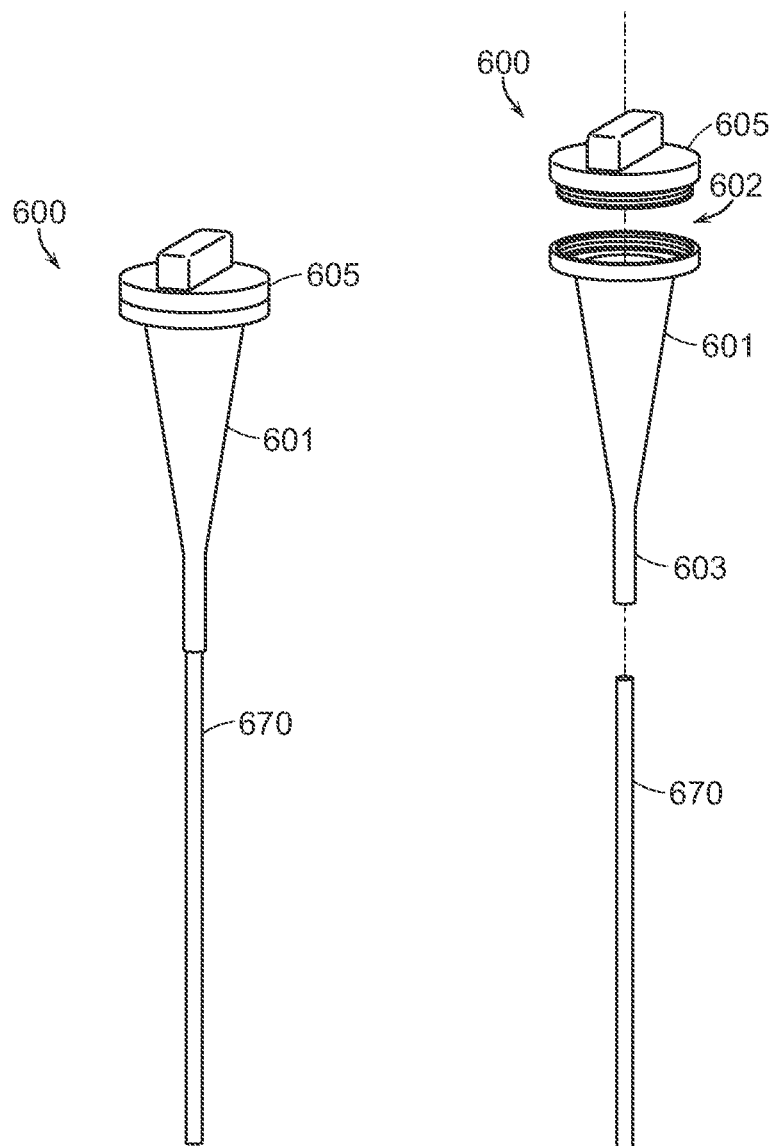
FIGS. 6A and 6B are isometric views of a funnel assembly for reducing a cross-sectional dimension of an expandable member in accordance with embodiments of the present technology.

FIGS. 6A and 6B are isometric views of a funnel assembly 600 configured in accordance with embodiments of the present technology. In particular, FIG. 6A is an isometric view of the funnel assembly 600 coupled to a sheath 670, and FIG. 6B is a partially exploded view of the funnel assembly 600 and the sheath 670. Referring to FIGS. 6A and 6B together, the funnel assembly 600 includes a body portion 601 and a cap 605. An opening 602 provides access to an interior of the body portion 601, which is generally cone-shaped and has a plurality of vanes (not shown) or other folding features. The body portion 601 also includes a relatively long and narrow distal end section 603. In some embodiments, the distal end section 603 is sized and shaped to interface with a sheath, such as the sheath 670 (which can be generally similar to the first introducer sheath 270, described above). For example, the distal end section 603 may fit within or otherwise penetrate a hemostatic valve inside the sheath 670.

The funnel assembly 600 can be used to automatically fold, twist, or otherwise decrease a dimension of an expandable member (e.g., the expandable member 110) to fit the expandable member into and through the sheath 670. In operation, the expandable member can be pulled through the body portion 601 of the funnel assembly 600 and into the distal end section 603. The vanes or other folding features can automatically fold, twist, or otherwise decrease a dimension of the expandable member as the expandable member is pulled through the body portion 601. The folded or twisted expandable member can then be pulled through the sheath 670. In the illustrated embodiment, the funnel assembly 600 is directly coupled to the sheath 670, although in other embodiments the funnel assembly 600 can be spaced apart from the sheath 670 and/or the expandable member can be loaded into the body portion 601 before inserting the funnel assembly 600 into the sheath 670. In some embodiments, lubrication (e.g., Viperslide®, Rotaglide™, etc.) can be added to the interior of the body portion 601 to make it easier to pull the expandable member through the body portion 601. Once the expandable member is in the body portion 601, the cap 605 can be connected to the opening 602 of the body portion 601 to reduce or minimize blood loss.

Figure 7A:
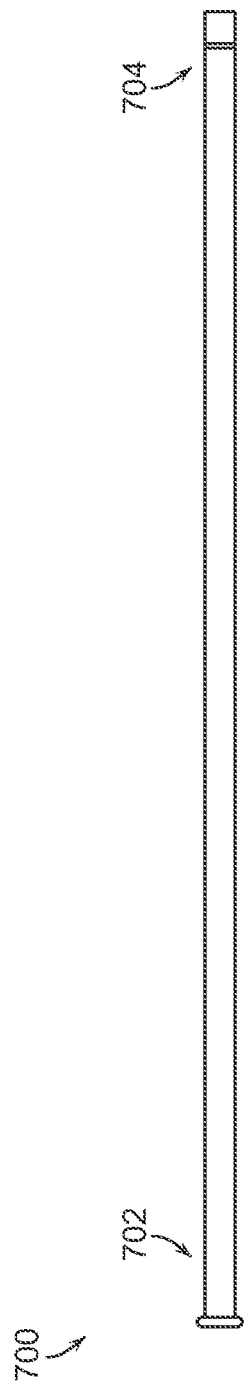
FIG. 7A is a side view of a folding tube for reducing a cross-sectional dimension of an expandable member in accordance with embodiments of the present technology.
Figure 7C:
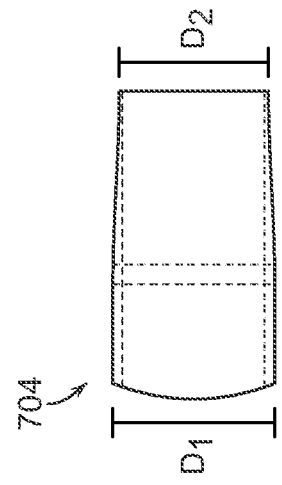
FIGS. 7B and 7C are enlarged side views of proximal and distal portions, respectively, of the folding tube of FIG. 7A configured in accordance with embodiments of the present technology.
Figure 7B:
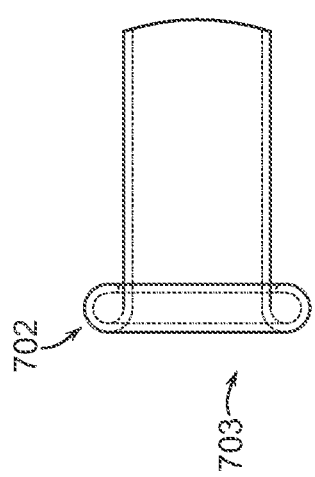

FIGS. 7A-7C illustrate a folding tube 700 configured in accordance with embodiments of the present technology. In particular, FIG. 7A is a side view of the folding tube 700, FIG. 7B is an enlarged view of a first end portion of the folding tube 700, and FIG. 7B is an enlarged view of a second end portion of the folding tube 700. Referring first to FIG. 7A, the folding tube 700 can be a generally elongated tube or shaft having a first (e.g., proximal or inlet) end portion 702 and a second (e.g., distal or outlet) end portion 704. Referring to FIG. 7B, the first end portion 702 includes an opening 703. The opening 703 is at least partially rounded or otherwise flared to prevent and/or reduce damage to an expandable member being pulled through the opening 703 and into the folding tube 700. Referring to FIG. 7C, the second end portion 704 is tapered such that it transitions from a first outer diameter $D_1$ to a second outer diameter $D_2$. The tapered second end portion 704 makes it easier to insert the folding tube 700 through a hemostatic valve in an introducer sheath, such as the first introducer sheath 270 described above. The tapered second end portion 704 can be inserted into an introducer sheath before loading the expandable member into the folding tube 700 or with the expandable member pre-loaded into the folding tube 700. The inner diameter of the folding tube 700 can remain substantially the same even though the outer diameter decreases.

The folding tube 700 can be used to fold, twist, or otherwise decrease a dimension of an expandable member (e.g., the expandable member 110) to fit the expandable member through an introducer sheath (e.g., the first introducer sheath 270). In operation, the expandable member can be loaded into the folding tube 700 by pulling the expandable member through the opening 703. In some embodiments, the expandable member can be manually twisted or otherwise folded before being pulled into the folding tube 700. With the expandable member in the folding tube 700, the second end portion 704 of the folding tube 700 is inserted into the introducer sheath. The expandable member is then pulled out of the second end portion 704 of the folding tube 700, through the introducer sheath, and into the patient's vasculature. In some embodiments, lubrication (e.g., Viperslide®, Rotaglide™, etc.) can be added to the interior of the folding tube 700 to make it easier to pull the expandable member through the folding tube 700. Once the expandable member is in the folding tube 700, a cap or other plug (not shown) can be inserted into the opening 703 to reduce or minimize blood loss when the folding tube 700 is inserted into the introducer sheath.

Figure 8A:
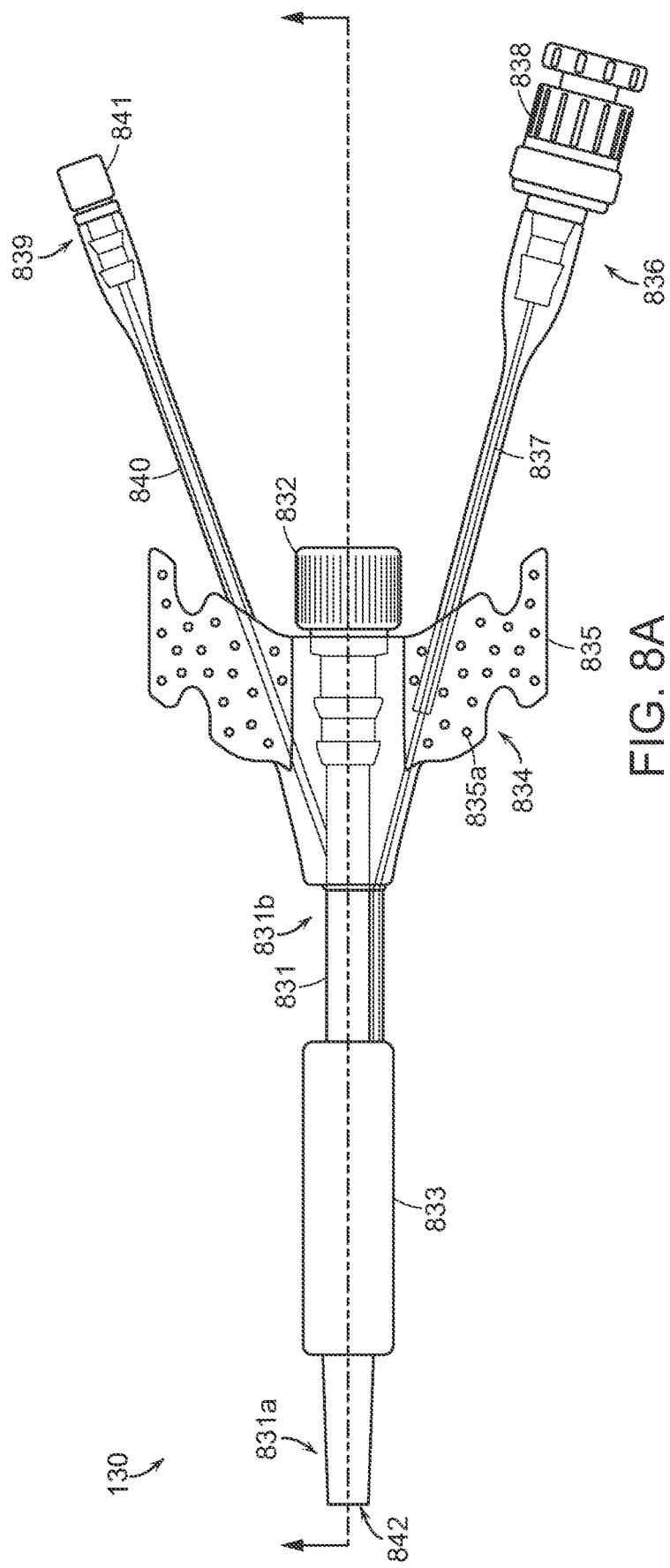
FIGS. 8A and 8B are side perspective and partial cross-sectional views, respectively, of an arterial interface device for establishing hemostasis configured in accordance with embodiments of the present technology.
Figure 8B:
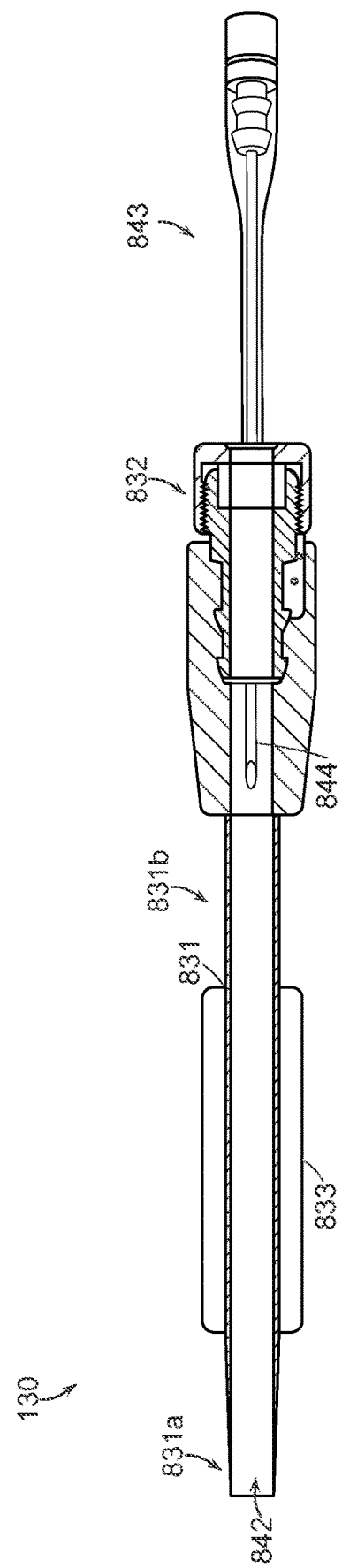

FIGS. 8A and 8B illustrate additional aspects of the stopper device 130 (also referred to as an "arterial interface device") configured in accordance with embodiments of the present technology. More specifically, FIG. 8A is a front view of the stopper device 130 and FIG. 8B is a cross-sectional view of the stopper device 130 taken along the axis indicated in FIG. 8A. Referring to FIGS. 8A and 8B together, the stopper device 130 includes a shaft 831 defining a first lumen 842 extending therethrough. The first lumen 842 has a diameter that is at least slightly larger than the outer diameter of the first driveline 120 such that the first driveline 120 can be inserted into and extend through the shaft 831, and/or such that the stopper device 130 can be deployed and/or advanced over the first driveline 120. The stopper device 130 further includes a fastening mechanism 832 that can secure the stopper device 130 to the first driveline 120 and provide a hemostatic seal therebetween. In some embodiments, the fastening mechanism 832 is a compression ring, a Touhy Borst valve, or the like. In some embodiments, the stopper device 130 can optionally include a driveline receiving element 843 inserted into the lumen at the fastening mechanism 832, as shown in FIG. 8B. The driveline receiving element 843 can include a channel 844 that extends at least partially into the lumen 842. To secure the first driveline 120 to the stopper device 130, the first driveline 120 can be advanced into and through the channel 844.

A distal end portion 831a of the shaft 831 can be tapered (e.g., inwardly tapered) to facilitate insertion of the stopper device 130 into an arteriotomy (e.g., as it is advanced over the first driveline 120) to provide hemostasis at the arteriotomy. The outer diameter of the distal end portion 831a therefore decreases moving in a proximal to distal direction. Thus, in operation, inserting the distal end portion 831a further into an artery can progressively dilate the arteriotomy to achieve hemostasis. In some embodiments, the distal end portion 831a also includes a marker (e.g., a radiopaque marker) that facilitates visualization of the distal end portion 831a via one or more imaging techniques.

The stopper device 130 can also include one or more anchoring mechanisms for securing the stopper device 130 in a desired orientation/position. For example, the stopper device 130 includes a first anchoring mechanism 833 (e.g., a distal anchoring mechanism). In the illustrated embodiment, the first anchoring mechanism 833 is an elastic and/or non-compliant expandable member (e.g., a balloon) able to be transitioned between a first deflated/unexpanded state (not shown) and a second inflated/expanded state (shown). When the stopper device 130 is positioned within the human body, inflating the first anchoring mechanism 833 causes the expandable member to inflate and press against surrounding tissue, thereby stabilizing the stopper device 130 near the arteriotomy. In some embodiments, the first anchoring mechanism 833 can include an adhesive element in addition to, or in lieu of, the expandable member. The first anchoring mechanism 833 can also take other suitable forms. For example, in some embodiments the first anchoring mechanism 833 is a plurality of barbs (e.g., expandable nitinol barbs), hooks, tabs, suture holes, or other features that can be used to stabilize or otherwise secure the stopper device 130 in a desired position.

As illustrated in FIG. 8A, the stopper device 130 can include a first side port 836 that permits a user to selectively inflate the first anchoring mechanism 833. The first side port 836 can include a second lumen 837 in fluid communication with an interior of the first anchoring mechanism 833. A valve or other stopper 838 (e.g., a check valve, a Luer lock, a sealable silicone port, etc.) can be included in the first side port to provide controlled access to the second lumen 837. To inflate the first anchoring mechanism 833 and anchor the stopper device 130, a gas or liquid (e.g., saline) can be injected into the first anchoring mechanism 833 via the first side port 836. For example, in some embodiments a syringe can be used to inject saline through the first side port 836 and into the first anchoring mechanism. Once inflated, the valve 838 can be closed. In some embodiments, the first anchoring mechanism 833 can remain inflated for a prolonged period (e.g., greater than about 1 year) as long as the valve 838 remains closed.

The stopper device 130 can further include a second anchoring mechanism 834 configured to be positioned exterior to a vessel and secured to tissue proximate to the arteriotomy. The second anchoring mechanism 834 can comprise one or more wings or other appendages 835 extending from the main stopper body, proximal to the first anchoring mechanism 833. The one or more wings or other appendages 835 can include a plurality of holes 835a. The stopper device 130 can be sutured to tissue using the holes 835a to stabilize and/or otherwise secure the stopper device 130 in a desired orientation/position.

When implanted over the first driveline 120 at the axillary artery, the stopper device 130 may need to be bent or flexed (e.g., towards the patient's abdomen) before being secured to the patient's tissue. Accordingly, at least a portion of the shaft 831 is at least partially flexible. For example, the shaft 831 may include a bendable region 831b between the first anchoring mechanism 833 and the second anchoring mechanism 834. A practitioner can manipulate the stopper device 130 into the desired orientation/position by bending or flexing the stopper at the bendable region 831b. Once in a desired orientation/position, the stopper device 130 can be secured in place using the first anchoring mechanism 833 and the second anchoring mechanism 834.

As illustrated in FIG. 8A, the stopper device 130 can further include a second side port 839. The second side port 839 provides access to a third lumen 840, which is in fluid communication with the first lumen 842 and enables a practitioner or other user to insert a wire into the patient's vasculature to facilitate device exchange, explant, or general control of the vasculature. For example, a practitioner can insert a wire through the second side port, through the third lumen 840, through the first lumen 842, and into the patient's vasculature. In such cases, the wire extends through the first lumen 842 external to and along a side of the first driveline 120 (e.g., between the first driveline 120 and the wall defining the shaft 831). In other embodiments, the third lumen 840 may extend along the length of the shaft 831 to the distal end portion 831a to provide an isolated channel for the wire. The second side port 839 can include a locking mechanism 841 for blocking access to the third lumen 840 when not in use. The locking mechanism 841 can be any suitable locking mechanism, including a plug, a cap (e.g., a Luer lock), an obturator, or the like.

EXAMPLES

Several aspects of the present technology are set forth in the following examples.

1. A method for implanting a circulatory support system into a patient's vasculature, the method comprising:
   accessing a first blood vessel of the patient;
   accessing a second blood vessel of the patient;
   advancing a guidewire through the patient's vasculature such that the guidewire extends between the first and second blood vessels;
   advancing an elongated delivery dilator over the guidewire such that the elongated delivery dilator extends between the first and second blood vessels, wherein a first portion of the elongated delivery dilator is externally accessible proximate to the first blood vessel and a second portion of the elongated delivery dilator is externally accessible proximate to the second blood vessel;
   releasably attaching the second portion of the elongated delivery dilator to a first end region of a driveline, wherein the driveline further includes a second end region attached to an expandable member;
   moving the second portion of the elongated delivery dilator, the driveline, and the expandable member through the patient's vasculature in a direction opposite that of blood flow while the first portion of the elongated delivery dilator is withdrawn from the patient until the expandable member is positioned within an aorta of the patient; and
   detaching the elongated delivery dilator from the first end region of the driveline after the first end region of the driveline exits the patient's vasculature proximate to the first blood vessel, wherein, following detachment, the expandable member and at least a portion of the driveline remain within the patient's vasculature to support heart function.

2. The method of example 1 wherein the first blood vessel is a subclavian artery or an axillary artery.

3. The method of example 1 or 2 wherein the second blood vessel is a femoral artery.

4. The method of any of examples 1-3 wherein:
accessing the first blood vessel comprises inserting a first introducer sheath in the first blood vessel, wherein the first introducer sheath includes a first hemostatic valve to provide controlled access to the first blood vessel; and
accessing the second blood vessel comprises inserting a second introducer sheath in the second blood vessel, wherein the second introducer sheath includes a second hemostatic valve to provide controlled access to the second blood vessel.

5. The method of example 4, further comprising:
removing the first introducer sheath from the first blood vessel; and
hemostatically sealing the first blood vessel around the driveline by advancing an arterial interface device over the driveline.

6. The method of example 4 or 5, further comprising:
removing the second introducer sheath from the second blood vessel; and
hemostatically sealing the second blood vessel.

7. The method of any of examples 1-6, further comprising removing a distal tip from the second portion of the elongated delivery dilator before releasably attaching the second portion of the elongated delivery dilator to the driveline, wherein removing the distal tip exposes a connection element.

8. The method of any of examples 1-7, further comprising folding, twisting, or otherwise decreasing a cross-sectional dimension of the expandable member before the expandable member moves into the patient's vasculature.

9. The method of example 8, further comprising pulling the expandable member through a funnel or tube before the expandable member is pulled into the patient's vasculature, wherein the funnel or tube automatically decreases the cross-sectional dimension of the expandable member.

10. The method of example 8 wherein folding, twisting, or otherwise decreasing the cross-sectional dimension of the expandable member comprises reducing an outer diameter of the expandable member.

11. The method of any of examples 1-10 wherein the expandable member is a balloon.

12. The method of any of examples 1-10 wherein the driveline is a first driveline, and wherein following detachment of the elongated delivery dilator from the first driveline, the method further comprises:
securing the first end region of the first driveline to a second driveline;
tunneling the second driveline through a subcutaneous region of the patient; and
securing the second driveline to a skin interface device.

13. The method of example 12 wherein the method further comprises removing a portion of the first end region of the first driveline before securing the first end region of the first driveline to the second driveline.

14. The method of example 12 wherein securing the first end region of the first driveline to the second driveline comprises placing a first driveline lumen extending through the first driveline in fluid communication with a second driveline lumen of the second driveline, and wherein the first and second driveline lumens are also in fluid communication with an interior of the expandable member.

15. The method of example 12, further comprising securing a portion of the second driveline to tissue of the patient.

16. A method for implanting a circulatory support system into a patient's vasculature, the method comprising:
accessing a subclavian artery of the patient;
accessing a femoral artery of the patient;
advancing a guidewire through the patient's vasculature such that the guidewire extends between the subclavian and femoral arteries;
advancing an elongated delivery dilator over the guidewire such that the elongated delivery dilator extends between the subclavian and femoral arteries, wherein a first portion of the elongated delivery dilator is externally accessible proximate to the subclavian artery and a second portion of the elongated delivery dilator is externally accessible proximate to the femoral artery;
releasably attaching the second portion of the elongated delivery dilator to a first end region of a driveline, wherein the driveline further includes a second end region attached to an end effector;
pulling the second portion of the elongated delivery dilator, the driveline, and the end effector through the patient's vasculature in a direction opposite that of blood flow while the first portion of the elongated delivery dilator is withdrawn from the patient until the end effector is positioned within a target site within the patient's vasculature; and
detaching the elongated delivery dilator from the first end region of the driveline after the first end region of the driveline exits the patient's vasculature proximate to the subclavian artery, wherein, following detachment, the end effector and at least a portion of the driveline remain within the patient's vasculature.

17. The method of example 16, further comprising:
advancing an arterial interface device over the first end region of the driveline after the first end region of the driveline exits the patient's vasculature proximate to the subclavian artery; and
establishing hemostasis at the subclavian artery using the arterial interface device.

18. The method of example 17, further comprising anchoring the arterial interface device to tissue proximate the subclavian artery.

19. The method of example 18 wherein anchoring the arterial interface device comprises inflating an expandable anchoring element on the arterial interface device.

20. The method of any of examples 16-19, further comprising removing a distal tip from the second portion of the elongated delivery dilator before releasably attaching the second portion of the elongated delivery dilator to the driveline, wherein removing the distal tip exposes a connection element.

21. The method of any of examples 16-20, further comprising folding, twisting, or otherwise decreasing a cross-sectional dimension of the end effector before the end effector moves into the patient's vasculature.

22. A system for intravascularly implanting a blood pump assembly into a patient, the system comprising:
an elongated delivery dilator having a first end portion, a second end portion, and a lumen extending between the first end portion and the second end portion, wherein the elongated delivery dilator is configured to advance over a guidewire positioned within the patient's vasculature and extend through the patient's vasculature between a first blood vessel and a second blood vessel; and a pump assembly including:
an expandable member configured to be positioned in a patient's descending aorta to provide circulatory support to the patient's heart; and
a driveline having a first end region connectable to the expandable member and a second end region connectable to the second end portion of the elongated delivery dilator.

23. The system of example 22 wherein the second end portion of the elongated delivery dilator includes:
a driveline connection element configured to releasably connect the elongated delivery dilator to the second end region of the driveline; and
a removable portion coupled to the driveline connection element,
wherein removing the removable portion from the elongated delivery dilator exposes the driveline connection element.

24. The system of example 23 wherein the removable portion is configured to direct the elongated delivery dilator through an introducer sheath.

25. The system of any of examples 22-24 wherein the first end region of the driveline includes an elongated delivery dilator connection element configured to releasably engage the second end portion of the elongated delivery dilator.

26. The system of any of examples 22-25 wherein the driveline includes an inner membrane, an outer membrane, and a kink-resistant element disposed between the inner membrane and the outer membrane.

27. The system of example 26 wherein the kink-resistant element is a helically wound nitinol coil.

28. The system of example 26 or 27 wherein the outer membrane comprises a biocompatible and anti-thrombogenic material.

29. The system of any of examples 22-28 wherein the driveline has a length that is greater than about 200 cm.

30. The system of any of examples 22-29 wherein the driveline has an outer diameter of about 4.2 mm or less.

31. The system of any of examples 22-30 wherein the expandable member is a balloon.

32. The system of example 31 wherein the balloon has an interior volume between about 20 mL and 60 mL.

33. The system of example 31 or 32 wherein the balloon has a proximal end portion connectable to the driveline and a distal end portion spaced apart from the proximal end portion, wherein at least a portion of the distal end portion is inwardly tapered.

34. The system of example 33 wherein the proximal end portion has a greater material thickness than the distal end portion.

35. The system of any of examples 22-34 wherein the expandable member comprises a biocompatible and anti-thrombogenic material.

36. The system of any of examples 22-35, further comprising a funnel assembly configured to fold, twist, or otherwise decrease a dimension of the expandable member.

37. The system of any of examples 22-36, further comprising a folding tube configured to fold, twist, or otherwise decrease a dimension of the expandable member.

38. The system of any of examples 22-37, further comprising an arterial interface device configured to provide a hemostatic seal with the first blood vessel.

39. The system of example 38 wherein the arterial interface device includes a shaft defining a first lumen extending therethrough for receiving a portion of the driveline, and wherein a distal end portion of the shaft is configured for placement within the first blood vessel.

40. The system of example 39 wherein the distal end portion of the shaft is tapered.

41. The system of example 38 or 39 wherein the arterial interface device includes an inflatable anchoring element coupled to the shaft proximate the distal end portion.

42. The system of any of examples 23-41 wherein the driveline is a first driveline, the system further comprising a second driveline connectable to the first driveline and configured to extend subcutaneously between the first driveline and a skin interface device.

43. The system of example 42 wherein the second driveline further comprises one or more wings, and wherein the one or more wings have one or more apertures.

44. The system of example 42 or 43 wherein the second driveline includes an absorptive feature configured to reduce longitudinal strain in the first driveline when the second driveline is connected to the first driveline.

45. The system of any of examples 42-44 wherein the second driveline has an internal diameter that is equal to or greater than an outer diameter of the first driveline.

46. The system of any of examples 42-45 wherein the first driveline has a distal segment including the first end region connectable to the expandable member and a proximal segment including the second end region connectable to the second driveline, and wherein at least a portion of the proximal segment is configured to be removed before the first driveline is connected to the second driveline.

47. A delivery system for intravascularly implanting a blood pump assembly into a patient, the delivery system comprising:
an elongated tubular element having a lumen extending therethrough and an end portion;
a connection element positioned at the end portion of the elongated tubular element and configured to releasably secure the elongated tubular element to a blood pump assembly driveline; and
a removable portion extending longitudinally from the end portion of the elongated tubular element and releasably coupled to the end portion of the elongated tubular element via the connection element,
wherein the elongated tubular member and the removable portion are configured to advance together over a guidewire positioned within the patient's vasculature and extend through the patient's vasculature between a first blood vessel and a second blood vessel.

48. The delivery system of example 47 wherein the removable portion is tapered in a direction away from the elongated tubular element to direct the elongated tubular element through an introducer sheath.

49. The delivery system of example 47 or 48 wherein the connection element is a first connection element, and wherein the removable portion has a second connection element configured to releasably engage the first connection element.

50. The delivery system of example 49 wherein the first connection element and the second connection element have a combined length less than about 2 cm when coupled together.

51. The delivery system of any of examples 47-50 wherein the connection element is a threaded connection element.

52. The delivery system of any of examples 47-51 wherein the connection element includes an aperture in fluid communication with the lumen.

53. The delivery system of any of examples 47-52, further comprising a kink-resistant element extending along at least a portion of the elongated tubular element.

54. The delivery system of example 53 wherein the kink-resistant element comprises at least one helically wound wire.

55. The delivery system of any of examples 47-54 wherein the elongated tubular element has a length greater than about 200 cm.

56. The delivery system of any of examples 47-55 wherein the elongated tubular element has a length of about 300 cm.

57. The delivery system of any of examples 47-56 wherein the elongated tubular element has an outer diameter of about 4.2 mm or less.

58. An arterial interface device for use with an implanted blood pump having a driveline extending through an opening in a blood vessel, the arterial interface device comprising:
- a shaft having a proximal end portion, a distal end portion, and a lumen extending between the proximal end portion and the distal end portion, wherein the distal end portion is tapered in a distal direction and configured for placement within the blood vessel, and wherein the lumen is configured to receive a portion of the driveline;
- a fastening mechanism configured to secure the driveline to the arterial interface device;
- an anchoring element proximate the distal end portion for securing the arterial interface device to tissue;
- wherein the arterial interface device is configured to provide a hemostatic seal with the blood vessel.

59. The arterial interface device of example 58 wherein:
the anchoring element is a first anchoring element,
the first anchoring element comprises a balloon configured to transition from an unexpanded state to an expanded state to secure the arterial interface device to the tissue; and
the arterial interface device further comprises—
- a first side port extending from the proximal end portion of the shaft and in fluid communication with to the anchoring element, wherein the first side port is configured to deliver fluid to the balloon to move the balloon to the expanded state;
- a second side port extending from the proximal end portion of the shaft and in fluid communication with the lumen, wherein the port is configured to receive a guidewire advanceable into the blood vessel; and
- a second anchoring element comprising one or more wings extending laterally outward from the shaft and having a plurality of holes configured to receive sutures that anchor the arterial interface device to adjacent tissue.

60. The arterial interface device of example 58 wherein the anchoring element is an expandable member configured to transition from an unexpanded state to an expanded state to secure the arterial interface device to the tissue.

61. The arterial interface device of example 60 wherein the anchoring element is a balloon.

62. The arterial interface device of example 60 wherein the anchoring element is one or more expandable barbs.

63. The arterial interface device of example 60 or 61, further comprising a side port in fluid communication with an interior of the expandable member, wherein the side port is configured to receive fluid for inflating the expandable member.

64. The arterial interface device of any of examples 58-63 wherein the anchoring element includes an adhesive element.

65. The arterial interface device of any of examples 58-64 the anchoring element is a first anchoring element, and wherein the arterial interface device further comprises a second anchoring element including one or more wings extending laterally outward from the shaft and having a plurality of holes configured to receive sutures that anchor the arterial interface device to adjacent tissue.

66. The arterial interface device of any of examples 58-65 wherein a portion of the shaft is at least partially flexible.

67. The arterial interface device of any of examples 58-66 wherein the distal end portion includes a marker visualizable through one or more imaging techniques.

68. The arterial interface device of any of examples 58-67, further comprising a port in fluid communication with the lumen, wherein the port is configured to receive a guidewire advanceable into the blood vessel.

69. A method for removing an intravascular assist device implanted within a patient's vasculature, the method comprising:
- advancing a distal portion of a wire through a driveline positioned within the patient's vasculature and into an interior volume of an expandable member coupled to a first end portion of the driveline, wherein the wire is advanced until a snaring element at the distal portion is adjacent a distal end portion of the expandable member;
- attaching an elongated delivery dilator to a second portion of the driveline external to the patient's vasculature via an affixation mechanism;
- accessing a second blood vessel at an access site downstream from the expandable member;
- advancing a capture mechanism into the second blood vessel, through the patient's vasculature, and towards the expandable member;
- grasping the expandable member with the capture mechanism by engaging the snaring element positioned within the expandable member;
- pulling the expandable member towards the access site via the capture mechanism and/or pushing the expandable member towards the access sheath via the elongated delivery dilator; and
- removing the expandable member from the patient's vasculature via the access site at the second blood vessel.

70. The method of example 69 wherein the first blood vessel is a subclavian artery or an axillary artery.

71. The method of example 69 or 70 wherein the second blood vessel is a femoral artery.

72. The method of any of examples 69-71 wherein:
accessing the second blood vessel comprises inserting a sheath into the second blood vessel; and
removing the expandable member from the patient's vasculature comprises advancing the expandable member at least partially into the sheath and removing the sheath containing the expandable member from the second blood vessel.

73. The method of any of examples 69-72 wherein:
accessing the second blood vessel comprises inserting a sheath into the second blood vessel; and
removing the expandable member from the patient's vasculature comprises advancing the expandable member through the sheath, and wherein the sheath remains in the second blood vessel following removal of the expandable member.

74. The method of any of examples 69-73 wherein the snaring element includes a ball or hook positioned at a distal end region of the wire.

75. The method of any of examples 69-74 wherein, after removing the expandable member from the patient's vasculature, a distal portion of the elongated delivery dilator extends through the access site, a medial portion of the elongated dilator extends through a portion of the patient's vasculature, and a proximal portion of the elongated delivery dilator extends out of the first blood vessel.

76. The method of example 75, further comprising:
   detaching the driveline and expandable member from the distal portion of the elongated delivery dilator;
   removably attaching a replacement driveline to the distal portion of the elongated delivery dilator, wherein the replacement driveline is secured to a replacement expandable member; and
   pulling the replacement driveline and replacement expandable member into the patient's vasculature by pulling the distal portion of the elongated delivery dilator towards the first blood vessel.

CONCLUSION

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. A system for intravascularly implanting a blood pump assembly into a patient, the system comprising:
   an elongated delivery dilator having a first end portion, a second end portion, and a lumen extending between the first end portion and the second end portion, wherein the elongated delivery dilator is configured to advance over a guidewire positioned within the patient's vasculature and to extend through the patient's vasculature between a first blood vessel and a second blood vessel; and
   a pump assembly including:
      an expandable member configured to be positioned in a patient's descending aorta to provide circulatory support to the patient's heart; and
      a driveline having a second end region connectable to the expandable member and a first end region connectable to the second end portion of the elongated delivery dilator.

2. The system of claim 1, wherein the second end portion of the elongated delivery dilator includes:
   a driveline connection element configured to releasably connect the elongated delivery dilator to the first end region of the driveline; and
   a removable portion coupled to the driveline connection element,
   wherein removing the removable portion from the elongated delivery dilator exposes the driveline connection element.

3. The system of claim 2, wherein the removable portion is configured to direct the elongated delivery dilator through an introducer sheath.

4. The system of claim 1, wherein the first end region of the driveline includes an elongated delivery dilator connection element configured to releasably engage the second end portion of the elongated delivery dilator.

5. The system of claim 1, wherein the driveline includes an inner membrane, an outer membrane, and a kink-resistant element disposed between the inner membrane and the outer membrane.

6. The system of claim 5, wherein the kink-resistant element is a helically wound nitinol coil.

7. The system of claim 5, wherein the outer membrane comprises a biocompatible and anti-thrombogenic material.

8. The system of claim 1, wherein the driveline has a length that is greater than about 200 cm.

9. The system of claim 1, wherein the driveline has an outer diameter of about 4.2 mm or less.

10. The system of claim 1, wherein the expandable member is a balloon.

11. The system of claim 10, wherein the balloon has an interior volume between about 20 mL and about 60 mL.

12. The system of claim 10, wherein the balloon has a proximal end portion connectable to the driveline and a distal end portion spaced apart from the proximal end portion, wherein at least a portion of the distal end portion is inwardly tapered.

13. The system of claim 12, wherein the proximal end portion has a greater material thickness than the distal end portion.

14. The system of claim 1, wherein the expandable member comprises a biocompatible and anti-thrombogenic material.

15. The system of claim 1, further comprising a funnel assembly configured to fold, twist, or otherwise decrease a dimension of the expandable member.

16. The system of claim 1, further comprising a folding tube configured to fold, twist, or otherwise decrease a dimension of the expandable member.

17. The system of claim 1, further comprising an arterial interface device configured to provide a hemostatic seal with the first blood vessel.

18. The system of claim 17, wherein the arterial interface device includes a shaft defining a first lumen extending therethrough for receiving a portion of the driveline, and wherein a distal end portion of the shaft is configured for placement within the first blood vessel.

19. The system of claim 18, wherein the distal end portion of the shaft is tapered.

20. The system of claim 18, wherein the arterial interface device includes an inflatable anchoring element coupled to the shaft proximate the distal end portion.

21. The system of claim 1, wherein the driveline is a first driveline, the system further comprising a second driveline connectable to the first driveline and configured to extend subcutaneously between the first driveline and a skin interface device.

22. The system of claim 21, wherein the second driveline further comprises one or more wings, and wherein the one or more wings have one or more apertures.

23. The system of claim 21, wherein the second driveline includes an absorptive feature configured to reduce longitudinal strain in the first driveline when the second driveline is connected to the first driveline.

24. The system of claim 21, wherein the second driveline has an internal diameter that is equal to or greater than an outer diameter of the first driveline.

25. The system of claim 21, wherein the first driveline has a distal segment including the second end region connectable to the expandable member and a proximal segment including the first end region connectable to the second driveline, and wherein at least a portion of the proximal segment is configured to be removed before the first driveline is connected to the second driveline.

* * * * *